US006495133B1

(12) United States Patent
Xue

(10) Patent No.: US 6,495,133 B1
(45) Date of Patent: Dec. 17, 2002

(54) *GLIOCLADIUM ROSEUM* STRAINS USEFUL FOR THE CONTROL OF FUNGAL PATHOGENS IN PLANTS

(75) Inventor: Allen G. Xue, Morden (CA)

(73) Assignee: Her Majesty the Queen in right of Canada, as represented by the Minister of Agriculture & Agri-Food Canada, Winnipeg (CA)

(*) Notice: Subject to any disclaimer, the term of this patent is extended or adjusted under 35 U.S.C. 154(b) by 0 days.

(21) Appl. No.: 09/407,285

(22) Filed: Sep. 29, 1999

Related U.S. Application Data

(60) Provisional application No. 60/102,582, filed on Sep. 30, 1998.

(51) Int. Cl.[7] .......... C12N 1/00
(52) U.S. Cl. .......... 424/93.5
(58) Field of Search .......... 424/93.5

(56) References Cited

U.S. PATENT DOCUMENTS

| | | | |
|---|---|---|---|
| 3,671,397 A | 6/1972 | Sih | 435/108 |
| 3,674,649 A | 7/1972 | Formisano et al. | 435/142 |
| 4,642,290 A | 2/1987 | Sih | 435/128 |
| 4,724,147 A | 2/1988 | Marois et al. | 424/93.5 |
| 4,818,530 A | 4/1989 | Marois et al. | 424/93.5 |
| 4,861,724 A | 8/1989 | Sih | 435/280 |
| 4,863,862 A | 9/1989 | Fukuda et al. | 435/166 |
| 4,866,081 A | 9/1989 | Ito et al. | 514/367 |
| 4,996,157 A | 2/1991 | Smith et al. | 424/93.5 |
| 5,068,105 A | 11/1991 | Lewis et al. | 424/93.3 |
| 5,085,999 A | 2/1992 | Bowers-Irons et al. | 435/264 |
| 5,165,928 A | 11/1992 | Smith et al. | 424/93.5 |
| 5,192,686 A | 3/1993 | Ahmad et al. | 600/431 |
| 5,194,258 A | 3/1993 | Paau et al. | 424/93.3 |
| 5,204,260 A | 4/1993 | Ahmad et al. | 424/256.1 |
| 5,273,749 A | 12/1993 | Bok et al. | 424/405 |
| 5,275,949 A | 1/1994 | Sakamoto et al. | 435/280 |
| 5,288,634 A | 2/1994 | Harman et al. | 435/254.1 |
| 5,300,127 A | 4/1994 | Williams | 47/57.6 |
| 5,334,517 A | 8/1994 | Matsuoka et al. | 435/121 |
| 5,403,584 A | 4/1995 | Crawford et al. | 424/93.43 |
| 5,407,826 A | 4/1995 | Matsuoka et al. | 435/254.1 |
| 5,415,672 A | 5/1995 | Fahey et al. | 47/57.6 |
| 5,527,526 A | 6/1996 | Crawford | 424/93.43 |
| 5,534,252 A | 7/1996 | McAfee et al. | 424/93.5 |
| 5,628,144 A | 5/1997 | Eastin | 47/581 R |

OTHER PUBLICATIONS

Baker, K. F. 1987. Evolving Concepts of Biological Control of Plant Pathogens. Ann. Rev. Phytopathol. 25:67–85.

Cook, R. J., and K. F. Baker. 1983. The nature and practice of biological control of plant pathogens. APS Press, St. Paul, MN. 539 pp.

Hwang, S. F., and P. Chakravarty. 1993. Integrated biological and chemical control of Rhizoctonia root rot of field pea by *Gliocladium virens* and a fungicide. J. Plant Dis. Prot. 100:308–316.

Parke, J. L., R. E. Rand, A. E. Joy, A. E. King. 1991. Biological control of Pythium damping–off and Aphanomyces root rot of peas by application of *Pseudomonas cepacia* or *P. fluorescens* to seed. Plant Dis. 75:987–992.

Nelson, E. B., G. E. Harman, and G. T. Nash. 1988. Enhancement of Trichoderma–induced biological control of Pythium seed rot and pre–emergence damping–off of peas. Soil Bio. Biochem. 20:145–150.

Windels, C. E., and T. Kommedahl. 1982. Pea cultivar effect on seed treatment with *Penicillium oxalicum* in the field. Phytopathology 72:541–43.

Oyarzun, P. J., J. Postma, A. J. G. Luttikholt, and A. E. Hoogland. 1994. Biological control of foot and root rot in pea caused by *Fusarium solani* with nonpathogenic *Fusarium oxysporum* isolates. Can. J. Bot. 72:843–852.

Xi, K., J. H. G. Stephens, and P. R. Verma. 1996. Application of formulated rhizobacteria against root rot of field pea. Plant Pathol. 45:1150–1158.

Steinmetz, J. and Schonbeck, F. 1994. Conifer bark as growth medium and carrier for *Trichoderma harzianum* and *Gliocladium roseum* to control *Pythium ultimum* on pea. Zeitschrift fur Pflanzenkrankheiten und Pflanzenschutzby 101:200–211.

Harman, E. E., I, Chet, and R. Baker. 1980. *Trichoderma hamatum* effects on seed and seedling disease induced in radish and pea by Pythium spp. or *Rhizoctonia solani*. Phytopathology 70:1167–1172.

Tu, J. C. 1992. Management of root rot diseases of peas, beans, and tomatoes. Can. J. Plant Pathol. 14:92–99.

Idemitsu Kosan Co Ltd: "Prevention of soil–borne diseases of plants– comprises adding Gliocladium fungi to culture soil" Derwent Publications Ltd., London, GB; AN 1997–029418.

(List continued on next page.)

*Primary Examiner*—Jean C. Witz
(74) *Attorney, Agent, or Firm*—Michael R. Williams; Adrian D. Battison; Ryan W. Dupuis

(57) ABSTRACT

A biocontrol agent and a method of use thereof for controlling diseases caused by fungal pathogens in plants. In one aspect of the invention, novel strains of *Gliocladium roseum* exhibiting antagonistic effects against plant pathogens are used as biocontrol agents. Most preferably, a novel strain *Gliocladium roseum* ACM941 (ATCC #74447) is used in a treatment effective against fungal pathogens of plants. The biocontrol agent of the present invention may be used in the treatment of seeds, soil or plants to effectively protect against plant diseases caused by fungal pathogens. The biocontrol agent is particularly effective against fungal infections of pea, bean, canola, wheat, barley, beet, broccoli, brussel sprouts, cabbage, canola, califlower, cucumber, egg plant, pepper, tomato, marigold and other horticultural and ornamental plants, caused by *Alternaria alternata, Aphanomyces euteiches,* Ascochyta spp., *Bipolaris sorokiniana, Fusarium graminearum, Fusarium oxysporum* f.sp. pisi, *Fusarium solani* f.sp. pisi, Fusarium spp. *Mycosphaerella pinodes,* Pythium spp., Rhizopus sp., *Rhizoctonia solani,* and *Sclerotinia sclerotiorum.*

26 Claims, 8 Drawing Sheets

OTHER PUBLICATIONS

Burgess: "Biocontrol of seedborne *Botrytis cinerea* in Chickpea with *Gliocladium roseum*", Biosciences Information Service, Philadelphia, PA, US, & Plant Pathology, vol. 46, No. 3, 1997, pp. 298–305.

Knudsen: "Biocontrol of seedling diseases of barley and wheat caused by *Fusarium culmorum* and *Bipolaris sorokiniana*: Effects of selected fungal antagonists on growth and yield components" Biosciences Information Service, Philadelphia, PA, US, & Plant Pathology, vol. 44, No. 3, 1995, pp. 467–477.

Idemitsu Kosan Co Ltd.: "Potato scab disease controlling agent–comprises fungus belonging to genus Gliocladium", Derwent Publications Ltd., London, GB; AN 1998–140878.

Tu, J.C. et al: "Comparison of several biological agents and benomyl in the control of Fusarium crown and root rot of tomatoes" Chemical Abstracts, vol. 122, No. 23, Jun. 5, 1995, Columbus, Ohio, US & Meded.–Fac. Landbouwkd. Toegepaste Biol. Wet. (Univ. Gent) (1994), 59(3A), 951–8.

Tu, J.C.: "Biological control of white mold in white bean using *Trichoderma viride, Gliocladium roseum* and *Bacillus subtilis* as protective foliar spray" & Meded. Fac. Landbouwk. Toegepaste Biol. Wetensch., vol. 62, No. 3b, 1997, pp. 976–986.

Sivapalan, A.: "Fungi associated with Broccoli seed and evaluation of fungal antagonists and fungicides for the control of seed– borne *Alternaria brassicicola*" & Seed Sci. Technol., vol. 21, No. 1, 1993, pp. 237–245.

Logan et al.: "Preliminary experiments with biological control of diseases of potato caused by *Rhizoctonia solani* in Northern Ireland" & Crop Protection in Northern Britain, 1984, pp. 120–125.

Fravel, D.R.: "Interaction of biocontrol fungi with sublethal rates of metham sodium for control of *Verticillium dahliae*", Chemical Abstracts, vol. 124, No. 21, May 20, 1996, Columbus, Ohio, US & Crop Prot. (1996), 15(2), 115–19.

King, E.B. and Parke, J.L. Biocontrol of Aphanomyces Root Rot and Pythium Damping–Off by *Pseudomonas cepacia* AMMD on Four Pea Cultivars. Plant Dis. 77:1185–1188.

Hwang, S.F. and Chakravarty, P. Potential for the integrated control of Rhizoctonia root–rot of *Pisum sativum* using *Bacillus subtilis* and a fungicide.

Herr, Leonard J. Biological control of Rhizoctonia spp; and hypovirulent *R. solani* agents. Crop Protection 1995, vol. 14, No. 3, 179–186.

Windels, C.E. Growth of *Penicillium oxalicum* as a Biological Seed Treatment on Pea Seed in Soil. Phytopathology 1981, vol. 9, 929–933.

Bailey, K.L. et al. Effects of tillage systems and crop rotations on root and foliar diseases of wheat, flax, and peas in Saskatchewan. 1992 Can. J. Plant Sci. 72: 583–591.

Slinkhard, A.E. et al. Biotic and abiotic stresses of cool season food legumes in the western heimsphere. 1994. Stresses in the Western Hemisphere. p. 195–208.

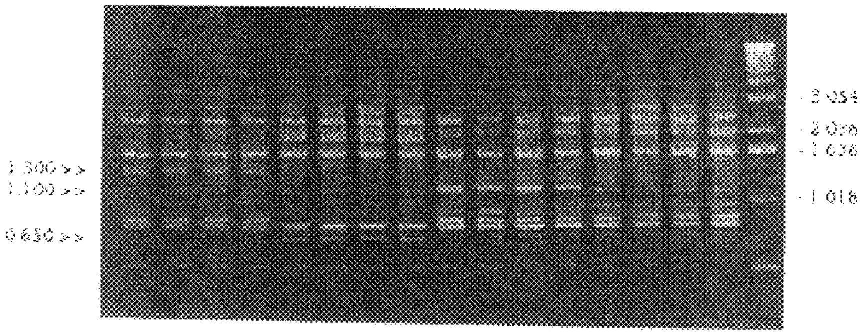

Fig. 1A

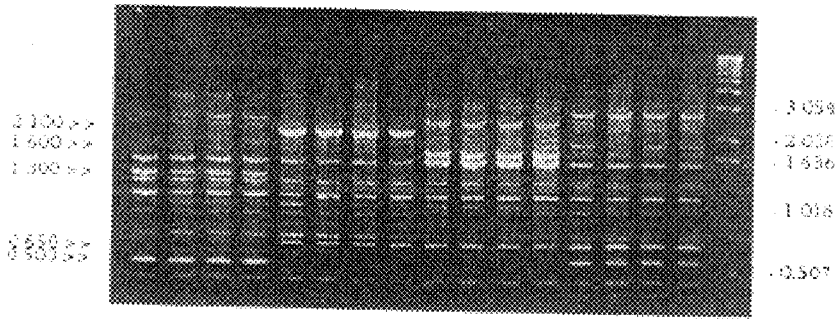

Fig. 1B

Random amplified polymorphic DNA (RAPD) analysis of genomic DNA from four isolates of *Gliocladium roseum* amplified with primer UBC 519 (A) and primer UBC 521(B). The products were separated on a 1% agarose gel. Lane 1-4 were four single spore cultures of ACM 941; lane 5-8 were four single spore cultures of DAOM 186891; lane 9-12 were four single spore cultures of DAOM 214827; lane 13-16 were four single spore cultures of DAOM 215746; and lane 17 was 1 kb DNA ladder.

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Decamer
      Oligonucleotide Primer.

<400> SEQUENCE: 1

accggacact                                                              10
```

-continued

```
<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Decamer
      Oligonucleotide Primer.

<400> SEQUENCE: 2

ccgccccact                                                          10
```

*GLIOCLADIUM ROSEUM* STRAINS USEFUL FOR THE CONTROL OF FUNGAL PATHOGENS IN PLANTS

CROSS-REFERENCE TO RELATED APPLICATIONS

This application claims the priority right of U.S. Provisional Application No. 60/102,582, filed Sep. 30, 1998.

BACKGROUND OF THE INVENTION

1. Field of the Invention

The present invention relates to a new strain of *Gliocladium roseum* fungus, referred to as ACM941 that is capable of controlling plant diseases. In particular, the present invention relates to the use of the new strain of *Gliocladium roseum* fungus as a biological control agent (sometimes referred to as bioagent) to inhibit soil-borne and seed-borne fungal pathogens and to enhance plant growth and productivity in both greenhouse and field conditions.

2. Description of Related Art

Soil-borne and seed-borne fungal pathogens of plants are responsible for severe economic losses in the agricultural and horticultural industries worldwide. These pathogens cause plant diseases such as seed decay, root/foot rot, seedling blight and wilt. Such diseases commonly reduce emergence, plant vigor and yield potential. Severe disease infection can kill emerging seedlings of an entire plant population, and result in a total loss of crop yield.

Solutions to the recurring problem of plant pathogens have been explored for decades. As particular crops become more abundant, and the area of land allocated for agriculture expands, there is an inherent need to employ more efficient and effective farming practices. As a result of increasing demand for crop production, farmers must often compromise their cultural practices by planting crops on sub-optimal land, or by increasing the frequency at which crops are planted in a specific location. In doing so, crop nutrients are depleted and specific crop pathogens, especially soil-borne or seed-borne pathogens, become more prevalent. Accordingly, it is increasingly difficult to sustain the health and productivity of a respective crop.

Historically, preferred cultural practices and chemical controls were used in combination to combat destructive pathogens. More recently, the use of integrated systems employing biocontrol agents and chemicals has become more prevalent.[1] (note: all superscript reference numerals relate to a list of references appearing at the end of this disclosure). However, despite progressive research in recent years, chemical alternatives remain the most reliable and economic solution to the problems caused by most soil-borne and seed-borne plant pathogens.

The case of field pea is illustrative. There were approximately 900,000 hectares of field pea in western Canada in 1998, estimated at a total farm value of over $400,000 million. In recent years, the field pea crops of western Canada have been most affected by soil-borne or seed-borne diseases, as well as the Ascochyta complexes of root and foliage. Known as PRRC (pea root rot complex) diseases, the soil-borne and seed-borne diseases are most commonly caused by the pathogens *Fusarium solani* f.sp. pisi, *Fusarium oxysporum* f.sp. pisi, *Mycosphaerella pinodes, Rhizoctonia solani, Sclerotina sclerotiorum, Aphanomyces euteiches, Alternaria alternata* and Pythium spp. The incidence of PRRC diseases varies with year and location, while its severity is largely dependent on climate, crop rotation and cultural practices. The yield losses of pea crops alone, as a result of PRRC pathogens including foliar infection by Ascochyta complex, are frequently devastating with a conservative 15% yield reduction translating into an approximate annual loss of $60 million in areas of western Canada. As crops such as pea become increasingly important, efforts must focus on more effective and efficient means of crop farming, both in Canada and around the world.

The most effective solution to the destruction of crop plants by pathogens would most likely be the development of resistant cultivars, which would allow for plant growth and productivity in the presence of fungal pathogens. Unfortunately, success in the development of PRRC resistant cultivars of pea, or other resistant crop cultivars, has not been forthcoming. Alternatively, biological control of crop plant pathogens by microorganisms may be considered a more natural and environmentally friendly alternative to existing chemical treatment methods. Accordingly, it is desirable to isolate a microorganism, which displays antagonistic effects against a target pathogen, and is capable of survival and propagation in a target location.

Efforts to isolate antagonistic microorganisms effective against plant pathogens have been underway in recent years. As a result, several microbial isolates have proven effective as plant pathogen antagonists and some related biocontrol products are currently commercially available, including: Mycostop™ (Streptomyces sp.); GleoGard™ (*Trichoderma virens*); Kodiak™ (Bacillus sp.); and BioTrek™ (Trichoderma sp.); TRICHODEX™ (*Trichoderma harzianum*); and BINAB-T™ (*T. harzianum* plus *T. polysporum*).

The effectiveness of bioagents against certain pathogens has been characterized according to a variety of modes of action. Cook et al.[2] described the modes by which a bioagent can effectively act against target pathogens as including: (i) a parasitic attack against the pathogen, (ii) a competitor for a common food source, (iii) a source of toxic antibiotic substances, or (iv) an induced indirect toxic effect by the release of volatile substances. As such, a bioagent behaves as a natural antagonist to the pathogen.

Although efforts have concentrated on the biological control of PRRC pathogens, obstacles in stability, delivery and versatility have not been resolved. Specifically, Hwang et al.[3] in 1992 reported the potential use of *Gliocladium virens* (Syn. *Trichoderma virens*) as a biocontrol agent against Rhizoctonia caused root rot in field pea, when employed with a fungicide. In this integrated control system, the presence of the fungicide provided protection against the pathogen when the environmental conditions inhibited the activity of the bioagent. Parke et al.[4] in 1991 disclosed findings of the effectiveness of *Pseudomonas cepacia* and *P. fluorescens* against Pythium damping-off and Aphanomyces root rot in pea when applied to seed. *P. cepacia* was disclosed as being the most effective bacterium, increasing emergence by an average of 40% and yield by 48% over captan fungicide alone. The Parke et al. reference further reported on disclosures of the effectiveness of seed treatment with species of Trichoderma[5] and *Penicilium oxalicum*[6] against diseases of pea Oyarzun et al.[7] further reported findings, in 1993, of the biological control of root rot in pea caused by *Fusarium solani,* with two nonpathogenic *Fusarium oxysporum* isolates. Both isolates of *F. oxysporum* investigated displayed reduced disease severity and prevented the plant weight losses owing to *F. solani* f. sp. pisi in sterilized soil. In 1996, Xi et al.[8] reported on the effectiveness of formulated Rhizobacteria against root rot of field pea. *Pseudomonas fluorescens* (strain PRA25) peat-based granular formulation increased yield by 17% over untreated, in a trial with light disease infection, and by 120% in another trial with moderate infection. *P. cepacia* (strain AMMD) and *P. fluorescens* increased seedling emergence, and decreased disease incidence and severity. However, these agents had variable effect on yield when disease level was light to moderate. In addition, biocoritrol agents resulted in only limited control when disease was severe. As a result, a commercially available microbial product for the treatment of root rot diseases of pea is not currently available.[8]

U.S. Pat. No. 5,165,928, issued on Nov. 24, 1992 to Cornell Research Foundation, Inc. and entitled "Biological Control of Phytophtora by Gliocladium", discloses the use of strains of *Gliocladium virens* (Syn. *Trichoderma virens*) on the root biosphere of plants in controlling plant diseases caused by *Phyrophthora sojae*. More specifically, this patent is directed to the use of specific strains of *T. virens* on *P. sojae*-caused stem and root rot in soybean plants.

Steinmetz and Schobeck[9] (1993), reported the use of conifer bark inoculum, comprising *Trichoderma harzianum* or *Gliocladium roseum*, in controlling *Pythium ultimum* on pea. Specifically, the applicability of conifer bark as a growth medium and inoculum carrier for *T. harzianum* or *G. roseum* was examined, as well as the antagonistic efficacy of such preparations to protect pea seedlings against pre-emergence damping-off caused by *P. ultimum*. This investigation looked at the possibility of using bark inoculum to control soil. borne pathogens in horticultural practice, and not specifically at the effectiveness of the respective fungal antagonist isolates. However, it was reported that a pretreatment with a nutrient solution was required on the *G. roseum*-containing bark inoculum for optimum development and efficiency of the antagonist. Accordingly, the *G. roseum* isolate investigated by Steinmetz and Schobeck is not easily or economically propagated for the treatment of seedlings.

Accordingly, the prior art has not disclosed a biocontrol agent effective against a variety of root rot pathogens, nor is there a bioagent, which can be economically and readily propagated for easy application to seeds or soil. Furthermore, a commercially effective biocontrol agent does not exist which can be applied to a seed or a suitable host, and provide prolonged effectiveness against a range of plant pathogens. In addition, there has not been previously disclosed a biocontrol agent, which, in the absence of an accompanying fungicide, is effective against a range of root rot pathogens including PRRC pathogens Pythium spp., *Fusarium solani* f.sp. pisi, *Fusarium oxysporum* f.sp. pisi, *Mycosphaerella pinodes, Rhizoctonia solani, Sclerotina sclerotiorum, Alternaria alternata,* and *Aphanomyces euteiches;* common root rot pathogen *Bipolaris sorokiniana;* and fursarium head blight pathogen *Fusarium graminearum.*

The lack of commercial development in the area of biocontrol products, and more specifically with respect to such products effective against root rot pathogens, may be largely in part due to the need for excessive amounts of the biocontrol agent, or, in the case of seed treatments, the short term effectiveness of the product.[10] In addition, the commercial availability of biocontrol agents against plant pathogens has been hampered by the lack of effective delivery systems.[11] The most successful biologically-based practices reported to date involve integrated management systems which employ a combination of biological, chemical and cultural control measures.[11] Accordingly, it is desirable to produce biocontrol agents which are effective against plant pathogens, under a variety of conditions and for a prolonged period of time. In addition, it is desirable to eliminate the need for chemical treatment in controlling root rot diseases in crop plants. More specifically, with respect to the present invention, it is desirable to produce an economically efficient biocontrol agent which can be readily propagated and applied to a plant source or growth medium to provide prolonged effectiveness against a range of PRRC pathogens. In addition, it is desirable to provide a biocontrol agent effective against a range of soil-borne and seed-borne pathogens in a variety of crop species.

BRIEF SUMMARY OF THE INVENTION

A main objective of the present invention is to provide a biological control agent effective against a variety of plant pathogens, and more specifically, to provide a biological control agent effective against PRRC pathogens of pea as well as other root pathogens of other plant species.

It is a further objective to provide an effective and commercially viable method of propagating the biological control agent of the present invention.

Further still, it is an objective of the present invention to provide a biological control agent which is at least as effective against plant pathogens as existing chemical alternatives, under appropriate conditions, and to provide an effective delivery system for said biological control agent.

It is a further objective of the present invention to provide an effective and commercially viable method of propagating the biocontrol agent of the present invention.

Another objective is to provide a delivery system for the effective application of the biocontrol agent of the present invention to a plant source or growth medium.

The present invention is based on the discovery and isolation of a novel strain of *Gliocladium roseum* Bainier, shown to have antagonistic effects against several plant pathogens, particularly root rot fungal pathogens in groups of Ascomycetes, Deuteromycetes, Oomycetes and Zygomycetes; as well as in a variety of host species in Asteraceae, Brassicaceae, Chenopodiaceae, Cucurbitaceae, Fabaceae, Poaceae and Solanaceae. For example, when applied to seeds of pea, the isolates of the present invention exhibit antagonistic capabilities against fungal pathogens that, in both controlled environments and field conditions, can be at least as effective as current chemical fungicides.

Thus, according to one aspect of the invention, there is provided a biologically pure culture of a strain of a microorganism *G. roseum* exhibiting antagonistic effects against a plant pathogen. Preferably, the strain of the microorganism is a strain ACM941 having the identifying characteristics of ATCC #74447 (please refer to the deposit information provided later).

According to another aspect of the invention, there is provided a composition a comprising: a culture of a strain of *G. roseum* (preferably ACM941) exhibiting antagonistic effects against a plant pathogen; and a delivery medium. e.g. a plant seed.

The invention also relates to seeds coated with a strain of the microorganism (preferably ACM941) and to methods of treating plants and plant seeds, etc., with the strain and compositions containing the strain.

According to a still further aspect of the invention, there is provided a method of propagating the strain of *G. roseum* (preferably ACM941) exhibiting antagonistic effects against fungal plant pathogens, which comprises incubating spores of said strain in a liquid medium for 3 to 5 days at a temperature in the range of 25° C. to 30° C. under low light intensity and pH≧4.5.

As described below, the strain of the present invention has been shown to display antagonistic effects against 13 pathogens including *Bipolaris sorokiniana, Fusarium graminearum, Fusarium oxysporum, Fusarium solani, Mycosphaerella pinodes* and *Sclerotinia sclerotiorum* representing the group of Ascomycetes; Ascochyta spp, *Rhizoctonia solani* and *Alternaria alternata* representing Deuteromycetes; *Pythium aphanidermatum, Pythium ultimum* and *Aphanomyces euteiches* representing Oomycetes; and Rhizopus sp. representing Zygomycetes. These 13 pathogens cause seed decay, root/foot rot, seedling blight and wilt on 17 crop plants including canola, broccoli, brussel sprouts, cabbage and cauliflower (Brassicaceae), field bean, field pea and sweet pea (Fabaceae), sugar beet and table beet (Chenopodiaceae), cucumber (Cucurbitaceae), marigold (Asteraceae), egg plant, pepper and tomato (Solanaceae), and wheat and barley (Poaceae). These are collectively referred to as pathosystems. In particular, these pathosystems are *Rhizoctonia solani* on pea (field pea and sweet pea), bean (dry bean and garden bean), beet (sugar beet and table beet), broccoli, brussel sprouts, cabbage, canola, cauliflower, cucumber, egg plant, pepper, tomato and marigold; *Sclerotinia sclerotiorum, Alternaria alternata, Fusarium oxysporum, Fusarium solani, Pythium aphanidermatum, Pythium ultimum, Aphanomyces euteiches,* Ascochyta spp., Rhizopus sp. and *Mycosphaerella pinodes* on pea; *Bipolaris sorokiniana* and *Fusarium graminearum* on wheat and barley. From these results, it is apparent that the strain of *G. roseum* has a broad effect on most or all fungal pathogens. The host plants appear to have little effect on the efficacy of ACM941 seed treatments in controlling fungal diseases, as shown by the effectiveness of the biocontrol agent against Rhizoctonia foot/root rot caused by *R. solani* in pea, bean, beet, broccoli, brussel sprouts, cabbage, canola, cauliflower, cucumber, egg plant, pepper, tomato and marigold. It is therefore predictable that the strain of *G. roseum* (ACM941) will control the same disease caused by the same pathogen in various field and horticultural crops, vegetables, and ornamental plants.

Besides the tested crops, Rhizoctonia root rot caused by *Rhizoctonia solani* is also a major disease that causes significant yield loss in Canada and worldwide in 589 genera of plants including field and horticultural crops, vegetables and ornamentals. Similarly, Sclerotinia rot or white mold caused by *Sclerotinia sclerotiorum* is also a very damaging disease of 177 genera of plants in the United States[21]; *Alternaria alternata* is a major pathogen of vegetables, field and horticultural crops and causes disease in 110 genera of plants; *Fusarium oxysporium* is a common wilt pathogen and causes significant damage in 156 genera of plants; *Fusarium solani,* Pythium spp. and *Aphanomyces euteiches* are common seed decay and root rot pathogens and cause diseases in 105, 92 and 8 genera of plants, respectively, *Bipolaris sorokiniana* is a common root rot and damping off pathogen and causes common root rot in 52 genera of plants; *Fusarium graminearum* is a common root rot and head blight pathogen in 18 genera of plants; and *Mycosphaerella pinodes* is a major pathogen of field pea and recorded in 6 genera of plants in the United States.

For the reasons given above, it is believed that the *G. roseum* strain of the present invention controls the diseases caused by the above pathogens in the indicated genus of plants. Thus, on the basis of the morphological characterization and mycoparasitic activity of the novel *G. roseum* strain herein disclosed, the effectiveness of this bioagent against fungal pathogens in a range of plant species, not just those herein specifically mentioned, is within the scope of the present invention. Specifically, the effectiveness of the *G. roseum* strain is not limited to the treatment of fungal pathogens in crop species, but also displays promise as a biocontrol agent of fungal pathogens in horticultural plant species, and other plants.

The primary strain of the present invention is *G. roseum* ACM941. However, it is further believed that other strains of *G. roseum,* particularly closely related isolates of *G. roseum* ACM941, display similar antagonist effects against fungal pathogens of plants. Such a additional strains, their compositions and methods of use are thus included within the scope of the present invention.

Thus, according to a first preferred aspect of the invention, there is provided a biologically pure culture of a microorganism *G. roseum* ACM941, having the identifying characteristics of ATCC #74447.

In accordance with another preferred aspect of the present invention, there is provided a composition comprising a culture of *G. roseum* ACM941; and a delivery medium.

In accordance with another preferred aspect of the present invention there is provided a coated seed comprising a coating of *G. roseum* ACM941.

In accordance with yet another preferred aspect of the present invention, there is provided a method for protecting a plant from fungal infection wherein the method comprises the steps of immersing plant seeds in a composition comprising *G. roseum* ACM941; and planting the seeds in a suitable growth medium.

In accordance with still another preferred aspect of the present invention, there is provided a method of protecting a plant from fungal infection comprising the steps of contacting said plant during a stage of the growth of said plant with a strain of a microorganism *Gliocladium roseum* exhibiting antagonistic effects against a fungal plant pathogen.

In accordance with still another preferred aspect of the present invention, there is provided a method of controlling fungal plant pathogens, comprising the steps of: providing a delivery medium comprising a culture of a strain of *Gliocladium roseum* exhibiting antagonistic effects against a fungal plant pathogen; and delivering said delivery medium to plants.

In accordance with a still further preferred aspect of the present invention, there is provided a method of enhancing the growth and productivity of plants comprising: providing a growth medium containing a strain of *Gliocladium roseum* exhibiting antagonistic effects against a fungal plant pathogen; and planting plant seedlings or seeds in said growth medium, The primary strain of the present invention has been determined to have a distinct genotype different from known strains of *G. roseum,* and a sample of the strain was deposited on behalf of Her Majesty the Queen in Right of Canada (as represented by the Minister of Agriculture and Agri-Food Canada) (the intended original assignee of the present application) under the terms of the Budapest Treaty at the American Type Culture Collection of 10801 University Blvd., Manassas, Va. 20110-2209, USA, on Jun. 2, 1998, under accession number ATCC #74447.

The use of the isolates of the present invention for the control of plant pathogens is highly favored over existing chemical alternatives in that it appears not to have adverse effects on non-target organisms, to cause harm to the environment, or to promote pathogen resistance. In the past, biological control agents have been unsuccessful as a result of their inability to propagate in certain soil environments and to promote their parasitic effect for sufficient durations of time. Further, fungal antagonists applied as a seed coating have not routinely colonized the plant rhizosphere.[1]

As already noted, the strain of the present invention displayed versatility in its effectiveness against a range of pathogens, as well as its ability to survive and proliferate in the plant rhizosphere, thus providing a target plant with prolonged protection against invasive pathogens.

In addition, the strain of the present invention can be readily propagated in a timely manner, in both solid media and relatively inexpensive liquid media, and applied as seed coatings without difficulty.

Moreover, the effectiveness of the isolates against a range of pathogens lends confidence in their ability to effectively protect a wide range of crops affected by other soil-borne and seed-borne fungal pathogens studied.

Preliminary studies have indicated the potential for the biocontrol ability of the *G. roseum* ACM941 strain against several major field crop, vegetable and ornamental diseases, including: rhizoctonia root/foot rot of peas, beans, beets, broccoli, brussel sprouts, cabbage, canola, cauliflower, cucumber, egg plant, pepper, and tomato; common root rot of wheat and barley; seed-borne phase of fusarium head blight of wheat and barley; Sclerotinia rot, ascochyta foot rot, fusarium root rot, fusarium wilt, aphanomyces root rot, pythium seed decay and root rot, seed-borne phase of alternaria blight, and seed-borne phase of mycosphaerella blight of field pea.

Studies of the broader applications of *G. roseum* ACM94 1 against plant pathogens continue to be conducted in western Canada. It is predicted that these studies will confirm that ACM941 is effective against other crops commonly afflicted by soil-borne and seed-borne fungal pathogens.

BRIEF DESCRIPTION OF THE DRAWINGS

FIG. 1A and FIG. 1B illustrate the DNA separation of ACM941 and three other *Gliocladium roseum* isolates on agarose gels;

DETAILED DESCRIPTION OF THE INVENTION

Figure 2A:
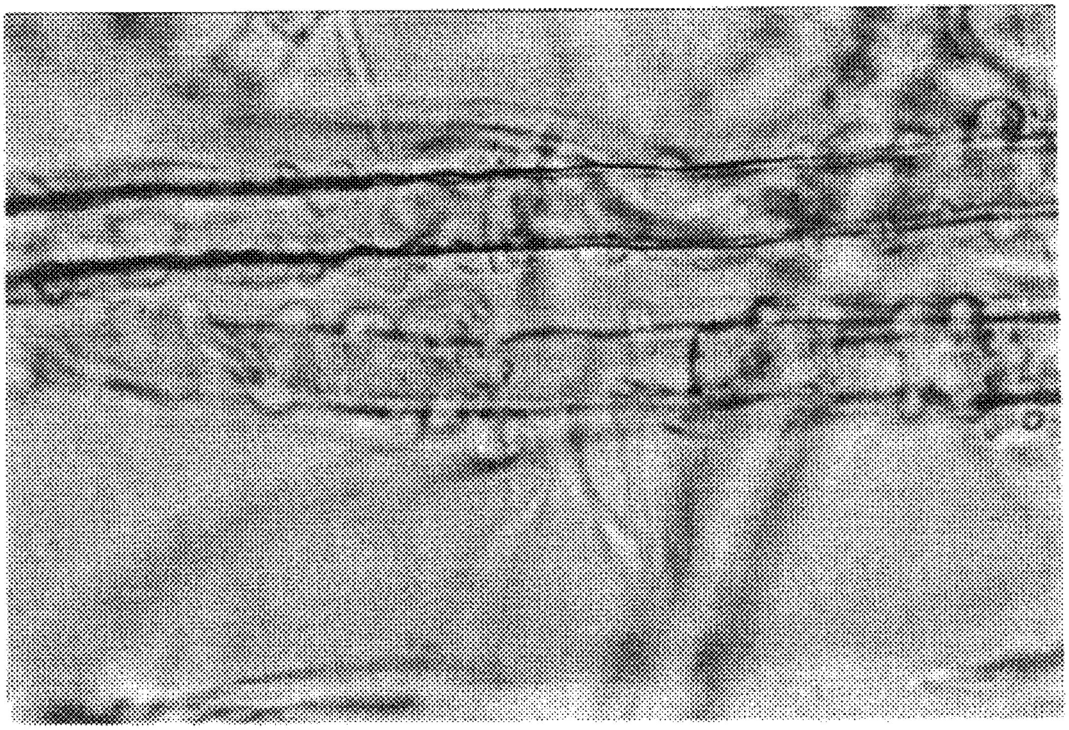
FIGS. 2A–2H illustrate the mycoparasitic activity of ACM941 against a variety of fungal pathogens.
Figure 2B:
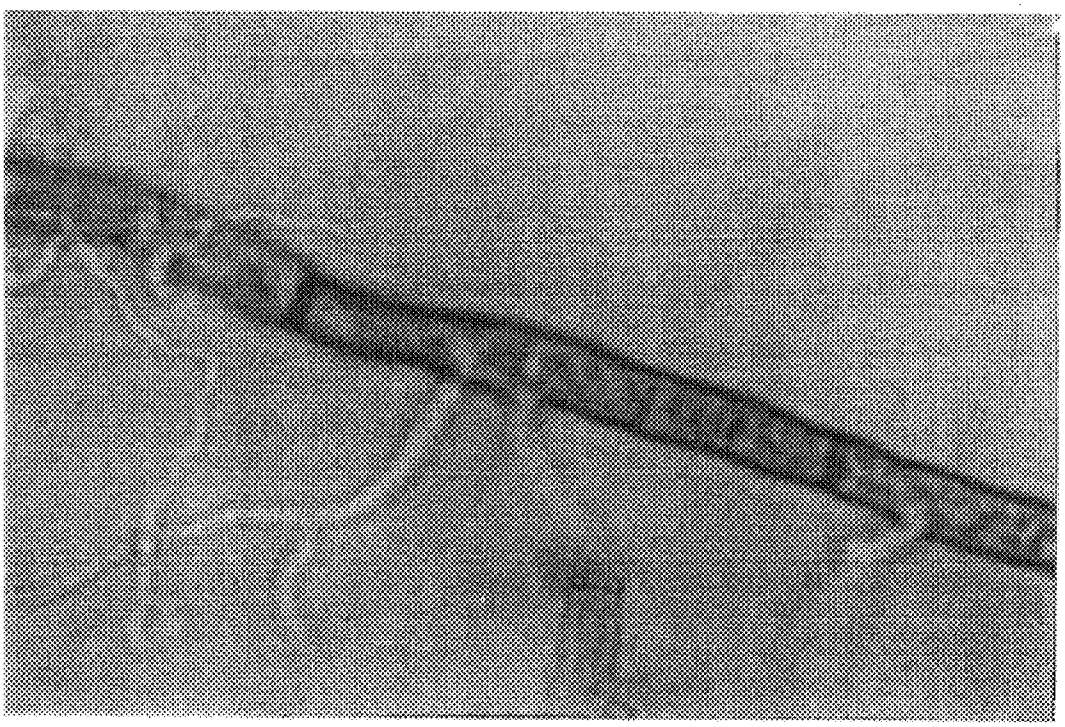
Figure 2C:
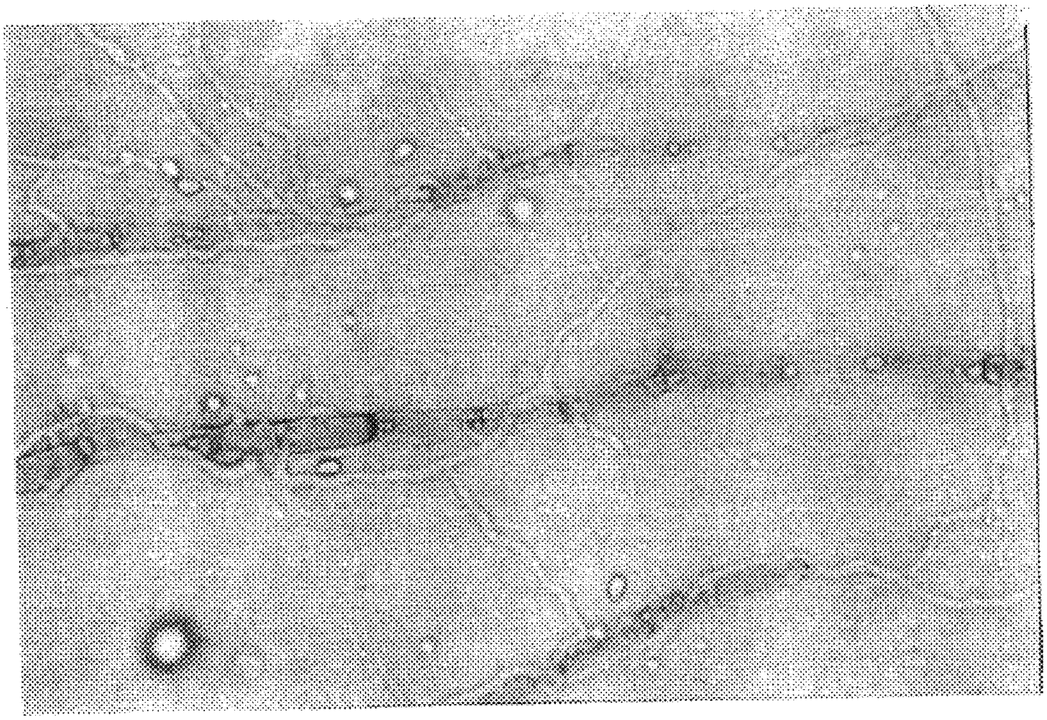
Figure 2D:
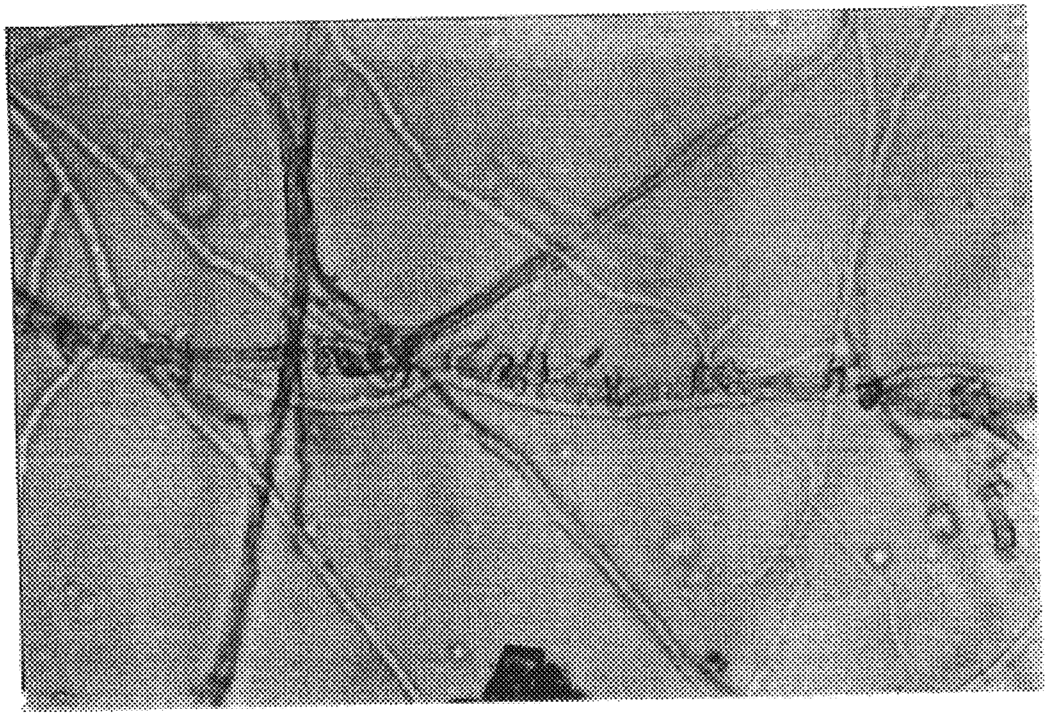
Figure 2E:
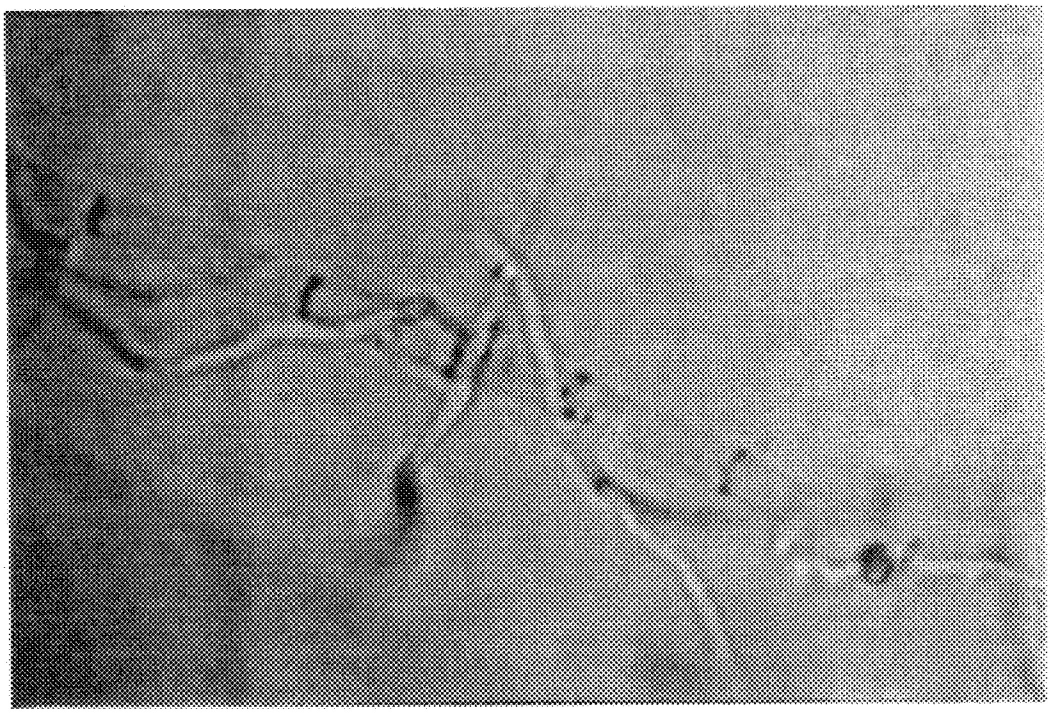
Figure 2F:
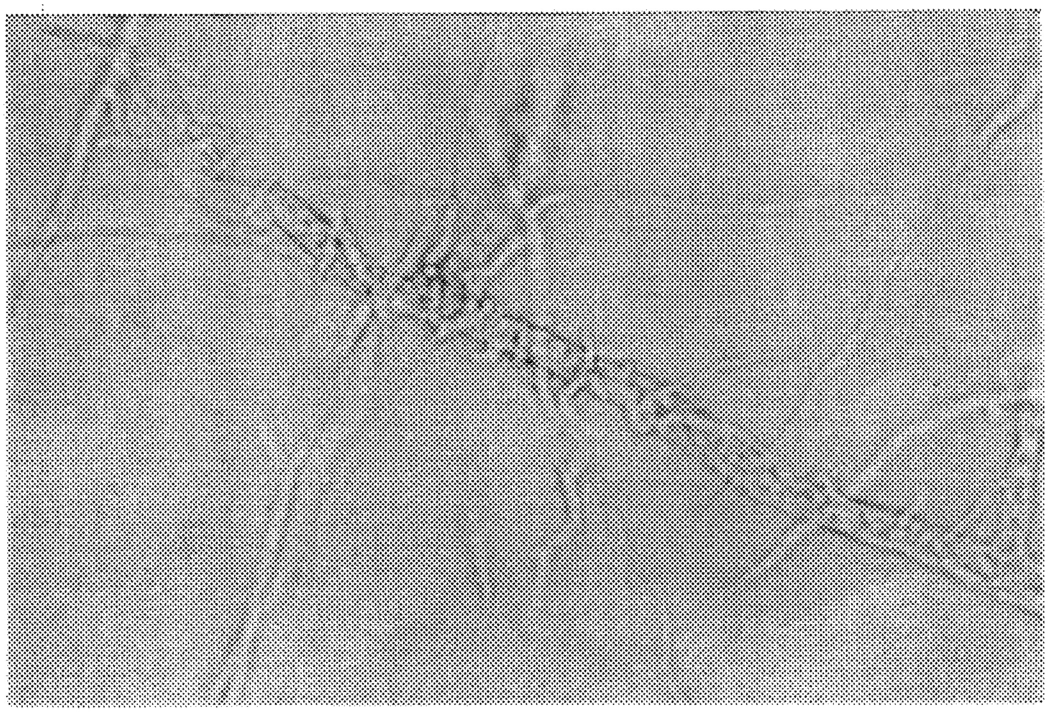
Figure 2G:
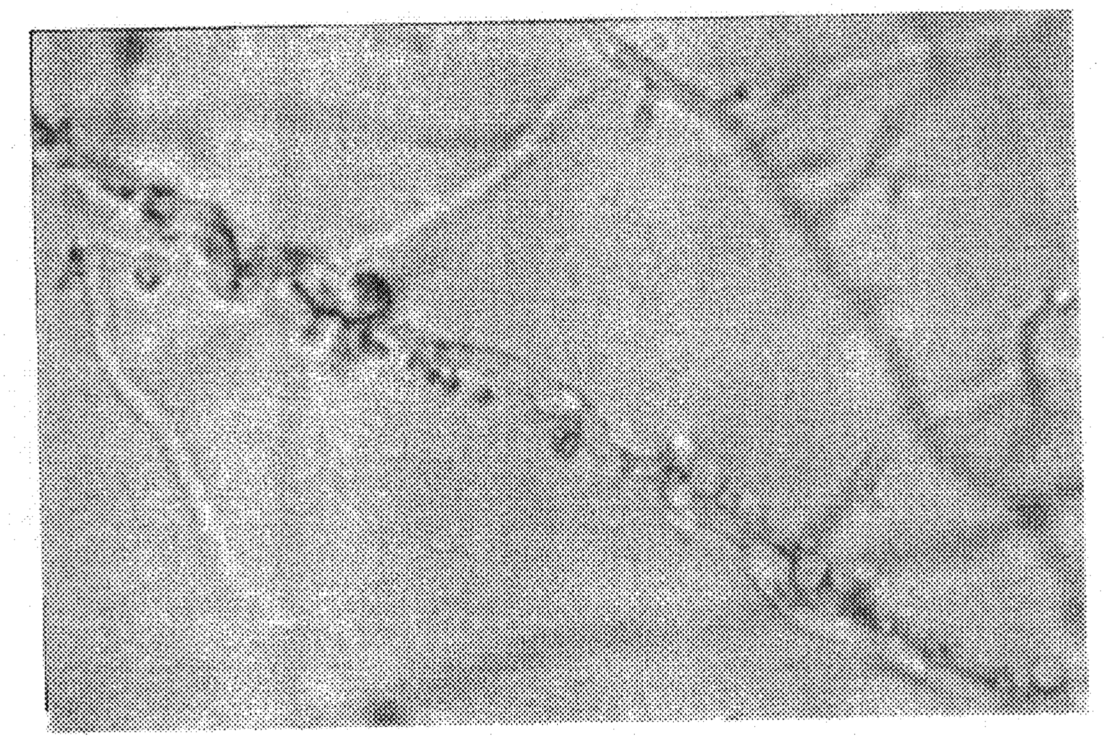
Figure 2H:
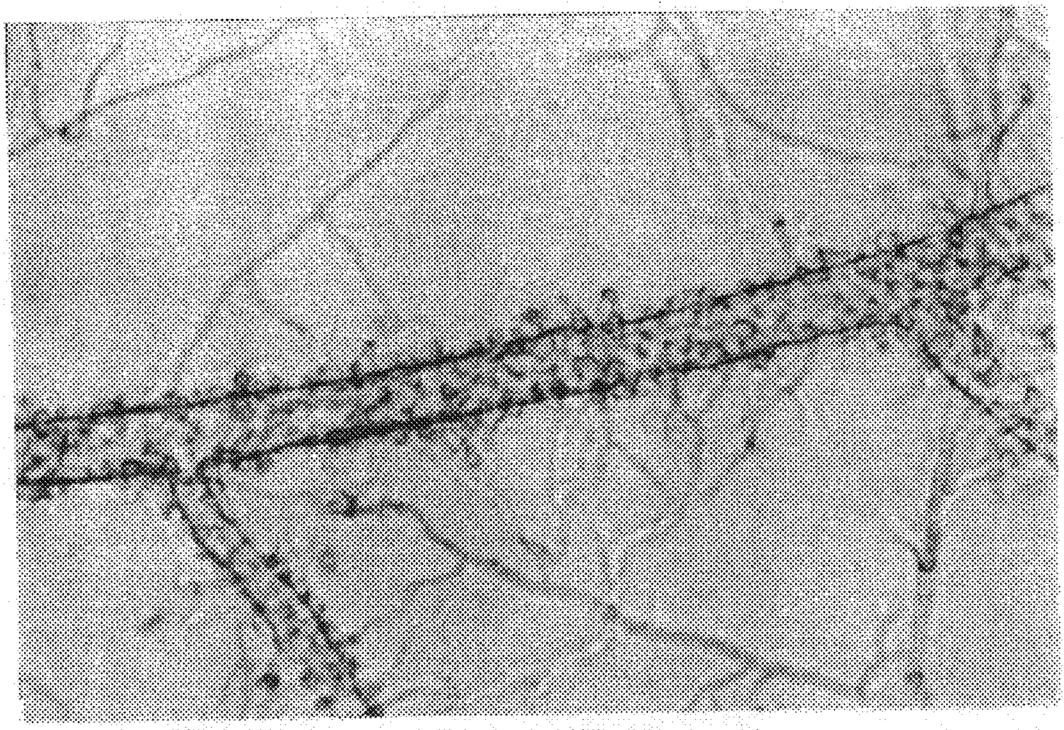

The present invention provides a biological control agent and delivery system, and methods for controlling root rot diseases in plants. This invention is particularly directed to the isolation of effective strains of the fungus *Gliocladium roseum,* and in particular to the isolation of a novel strain referred to as ACM941. This novel strain of *G. roseum* exhibits pronounced antagonist effects against a variety of fungal pathogens representing groups of Ascomycetes, Deuteromycetes, Oomycetes and Zygomycetes, known to cause root rot diseases in plants of Asteraceae, Brassicaceae, Chenopodiaceae, Cucurbitaceae, Fabaceae, Poaceae and Solanaceae. Specifically, the biological control agent of the present invention is effective in controlling plant diseases caused by *Alternaria alternata, Aphanomyces euteiches,* Ascochyta spp., *Bipolaris sorokiniana, Fusarium graminearum, Fusarium oxysporum* fsp. pisi, *Fusarium solani* f.sp. pisi, *Mycosphaerella pinodes,* Pythium spp., *Rhizoctonia solani,* Rhizopus sp., and *Sclerotina sclerotiorum.* Accordingly, ACM941 is herewith provided in particular as a biocontrol agent suitable for use against PRRC pathogens in field pea and those pathogens causing seed decay, root/foot rots, seedling blight and wilt in other crop plants.

The use of ACM941 in treating fungal pathogens causing PRRC diseases, root rots, and the seed-borne phase of fusarium head blight and mycosphaerella blight in plants is an effective alternative to existing chemical products, illustrating increased levels of efficacy, prolonged protection periods, a broader range of pathogenic targets and improved environmental safety. Similarly, ACM941 displays improved capabilities over previously disclosed bioagents effective against root rot pathogens of the pea plant. In addition to the effectiveness of ACM941 in treating fungal pathogens, this bioagent can be propagated in an economic and efficient manner.

ACM941 is shown to colonize in the plant rhizosphere, as well as proliferate with plant tissues as the target plant develops and grows. This characteristic highlights the advantage of ACM941 over chemical fungicides, which have a limited span of effectiveness, tend to accumulate in the environment and adversely affect non-target organisms. In addition, this confers an economic advantage in that only a limited quantity of the bioagent is required to achieve the desire effectiveness. Further, ACM941 is a relatively easy-to-use bioagent which readily propagates in both inexpensive simple liquid media and solid media and can be applied to seeds, soil or plants without difficulty.

ACM941 is also compatible with commonly used fungicides. An enhanced effect was generally observed when ACM941 was combined with metalaxyl or low rates of thiram fungicide.

The present invention provides a novel and useful alternative for treating and controlling PRRC and other plant pathogens. Specifically, ACM941 has been characterized as having a unique genotype and improved characteristics and mycoparasitic capabilities over existing biocontrol methods for the control of plaint pathogens known to cause such afflictions as seed decay, root/foot rots, seedling blight and wilt in a variety of plant species. Further, as most of the plant pathogens tested are common pathogens to a variety of field and horticultural crops, vegetables and ornamentals, it is within the scope of the present invention to suggest that the antagonistic effects of ACM941 may extend to the treatment of a variety of fungal diseases in a variety of plant species.

The ACM941 strain was first identified by the inventor of the present invention as a peach coloured growth of fungal mycelia on the surface of some lesions of a pea leaflet during a laboratory isolation of pathogens that cause ascochyta blight on field pea in 1994. The mycelia appeared on the plant tissue after approximately two days under moist chamber laboratory conditions. Close monitoring of the lesions revealed that ascochyta blight did not spread when in the presence of the peach coloured microbial growth, under the conditions of incubation, for up to five days. In contrast, those lesions absent of the microbial growths coalesced rapidly, resulting in leaf rot by the end of the five-day incubation period.

In view of the effects of the peach coloured growth, isolates were transferred to fresh medium and efforts to characterize the microbe were initiated. On the basis of the unique colony morphology and three DNA fingerprints differing from those of existing *Gliocladium roseum* deposits, the isolate was identified as having a novel genotype. These characteristics are illustrated in FIGS. 1A and 1B, and described in detail herein below. The distinguishing character of colony morphology of *G. roseum* ACM941 illustrated the lack of a concentric ring growth pattern on PDA medium. Further, the genetic characterization of the ACM 941 isolates illustrated differentiating bands of 1.3 kb with UBC519 primer, and 0.5 kb and 1.3 kb with UBC521 primer, in comparison with three other strains of *G. roseum,* namely DAOM 186891, DAOM 214827 and DAOM 215496, deposited with the Canadian Collection of Fungal Cultures, ECORC, Agriculture and Agri-Food Canada, Ottawa, Ontario.

Tests have shown that seed treatment with *G. roseum* ACM494 resulted in the control of PRRC diseases, increased emergence, greater fresh and dry weights of plants, better seedling stands and higher yield. More specifically, treatment of seeds of field pea increased emergence by an average of 13%, while yield was shown to increase by 14% over nontreated controls, based on two years of field evaluations in 10 separate field studies conducted in western Canada with eight PRRC pathogens including *A. euteiches, P. aphanidermatum, P. ultimum, F. oxysporum* f.sp. pisi, *F. solani* f.sp. pisi, *M. pinodes, R. solani,* and *S. sclerotiorum.* As such, the seed treatment of field pea with ACM941 bioagent was at least as effective as Thiram™ or Apron™, the only fungicides registered for use as a seed treatment for pea in western Canada at the time of the study.

Seed treatment with *G. roseum* ACM941 also controlled the seed-borne phase of fusarium head blight and common root rot in wheat and barley; and rhizoctonia root/foot rot in peas, beans, beets, broccoli, brussel sprouts, cabbage, canola, cauliflower, cucumber, egg plant, pepper, tomato and marigold. More specifically, treatment of seeds of these crops under artificial inoculation increased emergence by an average of 49%, fresh weight by 43%, dry weight by 61%. and reduced disease severity by 33%, over nontreated controls. These effects were equal to or greater than those achieved with registered fungicides.

As described in more detail below, the novel *G. roseum* ACM941 strain was found to be capable of propagating large amounts of spores (in the range of about $7\times10^6$ spores/mL) after 4–7 days of incubation at 20° C. in an inexpensive liquid medium such as malt extract broth. Alternatively, it was discovered that a maximum sporulation could be achieved after a 3–5 day incubation under 25° C.–30° C. conditions. The alternative incubation conditions are believed to be favoured under industrial conditions. It was further determined that high levels of light intensity (>40 $uEm^{-2}s^{-1}$) and a low initial pH (<4.5) of the medium have an inhibitory effect on the spore production of ACM941.

A further economic advantage of the present invention is the ability of the ACM941 bioagent to propagate within the plant rhizosphere as well as on plant tissues, when applied as a seed coating. In comparison to initial amounts of ACM941 applied to the seed coat of broccoli, carnation, field bean, field pea, tomato and wheat, the bioagent increased 5 to 1463-, 240 to 5160-, and 112 to 9173-fold, after 7, 21 and 35 days from seeding, respectively. ACM941 was also recovered from the epicotyl, primary roots and secondary roots after seed treatment of these crops, indicating that the bioagent propagated along with plant tissues as the plant developed. Accordingly, the propagation of the bioagent on the surface of plant tissues, as the plant develops and grows, indicates the ability of the bioagent to provide effective and long lasting protection against plant pathogens when applied to respective seeds. The ability of ACM941 to survive and propagate within the plant rhizosphere, as well as on the surface of plant tissues, further contributes to the economic efficiency of this bioagent in controlling plant pathogens.

Efforts to characterize the mycoparasitic action of the *G. roseum* ACM941 strain of the present invention revealed that the bioagent acts to entwine the hyphae of its target pathogens. Accordingly, without wishing to be bound to any particular theory, it is suggested that the antagonistic capabilities of *G. roseum* ACM941 strain are a result of such entwining action. Consequently, other strains of *G. roseum* that exhibit the same entwining effect are believed to be effective and within the scope of the present invention.

In addition to the effectiveness of the bioagent alone, an enhanced effectiveness was generally observed when ACM941 was applied as a seed treatment in combination with low rates of a fungicide, for example, thiram or motalaxyl. Such results suggest an alternative use of ACM941 for effectively controlling PRRC pathogens wherein the bioagent of the present invention is used in combination with a reduced amount of fungicide, to achieve results at least as effective as existing treatment methods under the appropriate conditions. Accordingly, there would be provided an effective method of controlling PRRC pathogens, while using a reduced amount of chemical fungicide in comparison with existing treatment methods.

A final product of the bioagent of the present invention may be freeze-dried or formed as concentrated spores in a sugar solution. The bioagent of the present invention may be used for coating seeds, treating soil or other growth mediums, or for direct application to plants to provide protection against infection by plant pathogens. The methods of propagating the microorganism of the present invention are described below. These methods may be scaled up to commercial levels using conventional liquid fermentation tanks or other conventional methods.

EXAMPLE 1

Isolation and Characterization of ACM941 Bioagent (1) Isolation and Identification The *G. roseum* ACM941 strain was discovered as a peach colored growth of fungal mycelia on the surface of some lesions of a pea leaflet during a laboratory isolation of pathogens that cause ascochyta blight on field pea at Agriculture and Agri-Food Canada (AAFC) Research Centre, Morden, Manitoba, Canada in May 1994. The peach coloured growths appeared on the plant tissue after approximately two days under moist chamber laboratory conditions. Close monitoring of the lesions revealed that the ascochyta blight pathogens did not produce spores on the leaf surface and the lesions did not spread when in the presence of the peach coloured growth, under the conditions of incubation, for up to five days. In contrast, those lesions absent of the growths coalesced rapidly, resulting in abundant sporulations of the ascochyta blight pathogens and leaf rot by the end of the five-day incubation period. This phenomenon suggested that the peach coloured fungal mycelia growth might have had a strong antagonistic interaction toward the pathogens of ascochyta blight. The fungal mycelia growth was thereafter transferred to a potato dextrose agar medium (PDA) and seven single spore cultures were initially. These cultures were morphologically identical and only one strain designated as ACM941 was further evaluated for the biological control of plant pathogens.

Taxonomy of ACM941 was conducted according to standard mycological tests.[12, 13] ACM941 was identified as *Gliocladium roseum* Bainier based on the formation of two distinct types of conidiophores, penicillate branch and verticillate branch.[14, 15, 16, 17, 18] The identification of ACM941 as *G. roseum* was confirmed by Dr. K. Seifert, Mycologist, Agriculture and Agri-Food Canada, National Identification Service, Biological Resources Research, ECORC, Ottawa, Ontario, in February 1995.

(2) Unique Morphological and Cultural Characteristics

The morphological and cultural characteristics of ACM941 bioagent were examined in comparison with three type cultures of *G. roseum* isolates, namely DAOM 18689, DAOM 214827, and DAOM 215496. These cultures were deposited at the Canadian Collection of Fungal Cultures, ECORC, Agriculture and Agri-Food Canada, Ottawa, Ontario. The isolates were compared for growth and cultural characteristics in six different agar media in 9-cm diameter Petri dishes. The media tested were Czapek's, 1.5% malt extract, 2% water agar, PDA Sigma (Sigma PDA 39.0 g, distilled water 1 L), PDA nature (white potatoes 500 g, glucose 20 g, agar 15 g, distilled $H_2O$ 1 L), and V-8 juice agar. Colony diameter was measured with vernier calipers at 3, 7, 14 and 21 days after inoculation. Description of colony characteristics was made at 14 days after inoculation. Conidiophore, conidial spore and phialide sizes were measured by growing the isolates on 2% water agar 6 days after inoculation.

Compared to the three type cultures of *G. roseum,* the ACM941 strain was intermediate in growth rate on all six media used, with colony diameter ranging from 9.7 to 12.9 mm, 22.3–38.9 mm, 39.3–77.6 mm and 52.6–85.0 mm when measured at 3, 7, 14 and 21 days after inoculation, respectively. In addition, the ACM941 strain was intermediate in conidiophore, conidium and phialide sizes, with conidiophore ranging from 76.1–110.0×3.0–3.3 $\mu$m, conidium ranging from 6.0–7.1×2.7–2.8 $\mu$m, and phialide ranging from 23.3–30.6×2.5–2.7 $\mu$m.

Colony morphology of the ACM941 stain was different from the three type cultures of *G. roseum* by not forming a concentric ring pattern on both PDA (Sigma) and PDA (nature) media, but identical with the type cultures on the other media tested.

(3) Genetic Characterization

Genetic composition of the ACM941 strain, in comparison with the three type cultures of *G. roseum,* DAOM 186891, DAOM 214827 and DAOM 215496, was analyzed in accordance with the protocol for random amplified polymorphic DNA analysis (RAPD). From each of these original cultures, four single-conidial isolates were derived and used in the present study. DNA was extracted from these isolates using the method of Lee and Taylor (1990).[19] Decamer oligonucleotide primers obtained from the University of British Columbia, Vancouver, BC, Canada were used with the RAPD analysis. RAPD reactions were performed in a PTC-100 (Trademark) MJ Research Programmable thermal controller. (Gibco BRL, Gaithersburg, Md.). Gels were subsequently stained with Ethidium Bromidc in order to visualize the DNA bands, and photographs were taken using a MP4 Land Camera™ with 667 black and white film (Polaroid Corp., Cambridge, Mass.) under UV light.

A total of 33 random sequence decamer primers were screened for DNA polymorphisms among the isolates of *G. roseum.* Of these, primers 519 (nucleotide sequence ACC GCA CAC T) and 521 (nucleotide sequence CCG CCC CAC T) produced simple banding patterns that revealed DNA polymorphisms among the isolates (FIG. 1). The two primers resulted in the detection of eight reproducible amplification products (RAPD markers) from the four *G. roseum* cultures, but not among the four single spore isolates used for each culture. With primer 519, ACM941 isolates had a differentiating band of 1.3 Kb size, DAOM 186891 had a band of 0.65 Kb and DAOM 214827 had a band of 1.1 Kb size. These three bands were not apparent in the DAOM 215746 isolate, making it different from the other cultures. With primer 521, ACM941 had two differentiating bands of 1.3 Kb and 0.5 Kb in size; DAOM 186891 had a unique band of 2.1 Kb; DAOM 214827 had a 1.6 Kb band; and DAOM 215746 had a 0.6 Kb band. Accordingly, on the basis of the above results, it was determined that each of the four *G. roseum* cultures were genetically distinct. Specifically, ACM941 illustrated a unique pattern for the two primers selected, compared to the other three type cultures of *G. roseum.*

(4) ATCC Accession Number

A deposit of ACM941 bioagent, as a unique strain of *Gliocladium roseum* Bainier, was made under the terms of the Budapest Treaty with the American Type Culture Collection (ATCC), 10801 University Blvd., Manassas, Va. 20110-2209, USA, on Jun. 2, 1998. ACM941 has been designated ATCC Accession #74447.

EXAMPLE 2

Mycoparasitic Activities of ACM941 Bioagent

ACM941 was evaluated for mycoparasitism to eight major root rot fungal pathogens including *Pythium aphanidermatum, Alternaria alternate, Fusarium oxysporum* f.sp. pisi. *Mycosphaerella pinodes, Rhizoctonia solani, Aphanomyces euteiches, Fusarium solani* f.sp. pisi., and *Sclerotina sclerotiorum.* These pathogens were isolated from naturally infected plants in 1997. *P. aphanidermatum* and *A. euteiches* fungi were grown on a Difco™ corn meal agar (CMA) medium, and the other pathogens and the ACM941 bioagent were grown on potato dextrose agar (PDA). Mycoparasitism was examined with paired grows of ACM941 bioagent and individual pathogens in 9 cm diameter Petri dishes. Each Petri dish was inoculated with each of a 5-mm diameter mycelium disk of ACM941 and pathogen. A strip of cellophane membrane, cut to 20×20 mm, was autoclaved and placed between the bioagent and pathogen in each plate. The mycelium disks were placed 1–2 cm away from the cellophane membrane, depending on the growth speed, to ensure that the organisms intersected near the middle of the cellophane strip. Inoculated plates were incubated at 20° C. under a 12 hour light/dark cycle at 24 $uEm^{-2}s^{-1}$ light intensity.

The cellophane membrane strips were removed from the surface of the media, placed on microscopic slides and examined for characteristics of mycoparasitic activity when mycelium intersections had occurred. Cellophane strips were stained with 0.2% Tryptan blue to aid in the visibility of mycelia. Examination was conducted under an objective light microscope and mycoparasitic manifestations were photographed using a Nikon camera with 160 Tungsten positive film (Kodak).

Mycoparasitic characteristics of ACM941 were observed on all eight fungal pathogens tested. The mycoparasitism of ACM941 on mycelium of *R. solani, A. alternata, M. pinodes, P. aphanidermatum, S. sclerotiorum, F. oxysporum* f. sp. pisi, *F. solani* f. sp. pisi and *A. euteiches* is illustrated in FIGS. 2A–H.

Figure 3:
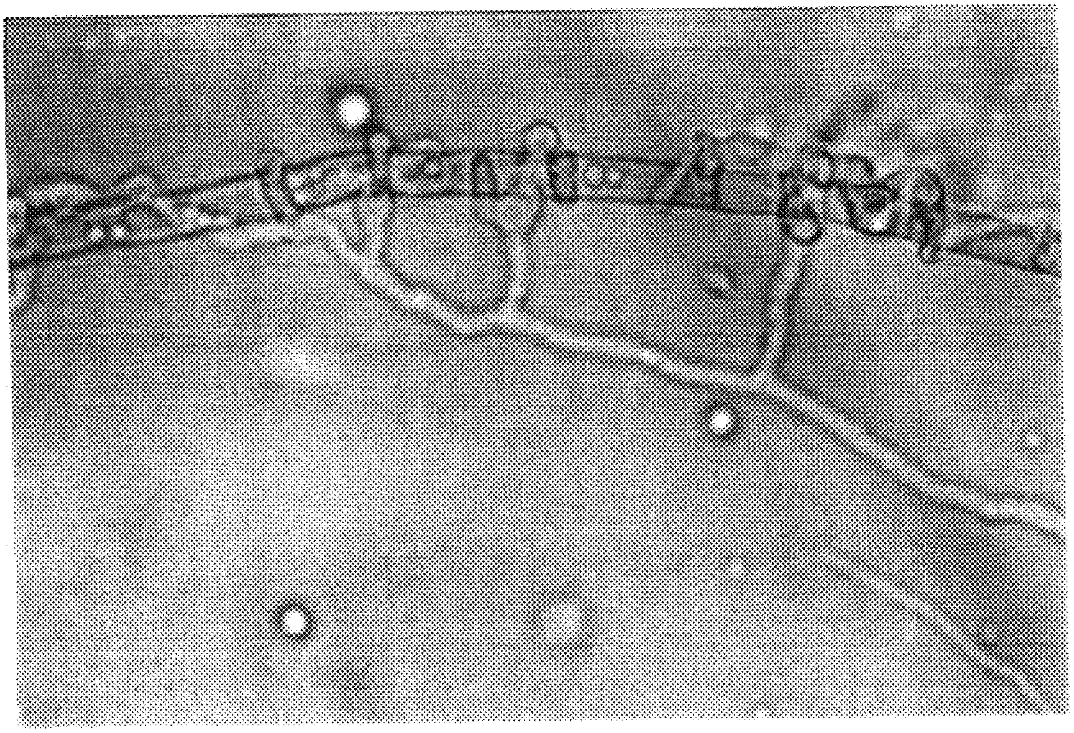
FIG. 3 illustrates a photograph depicting the lateral hyphae branches of ACM941 entwining and killing a pathogen mycelium.
Figure 4A:
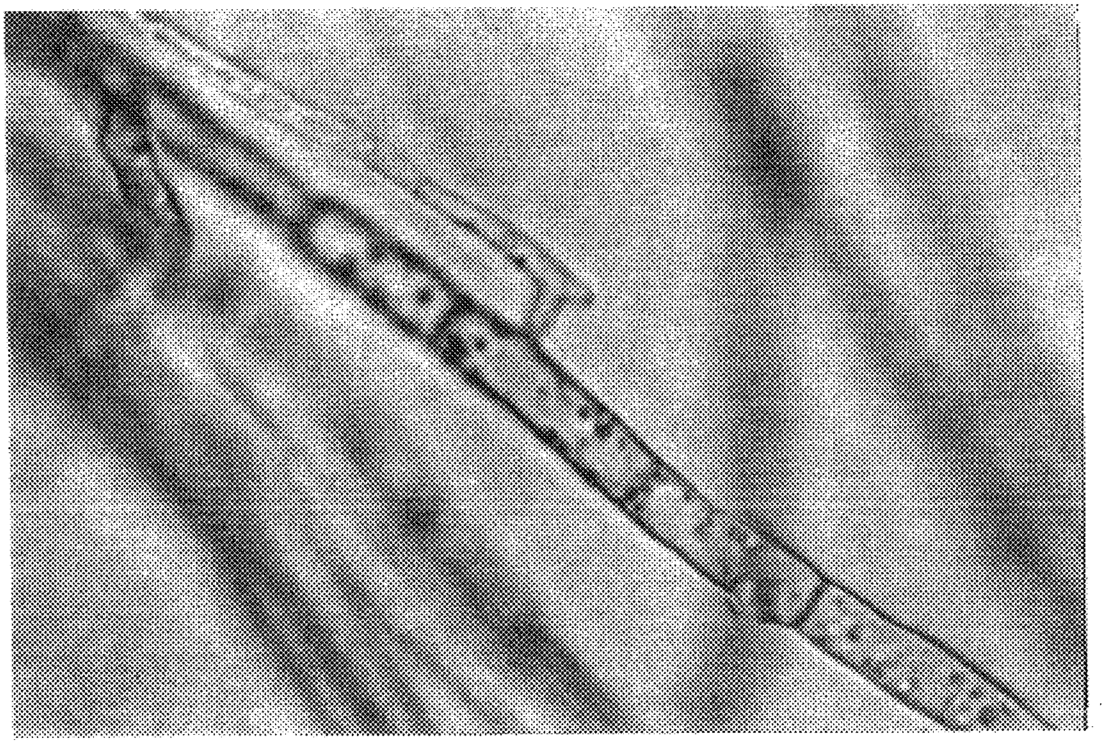
FIG. 4A and FIG. 4B illustrate the penetration (FIG. 4A) and internal growth (FIG. 4B) of ACM941 hyphae in a mycelium of *A. alternata.
Figure 4B:
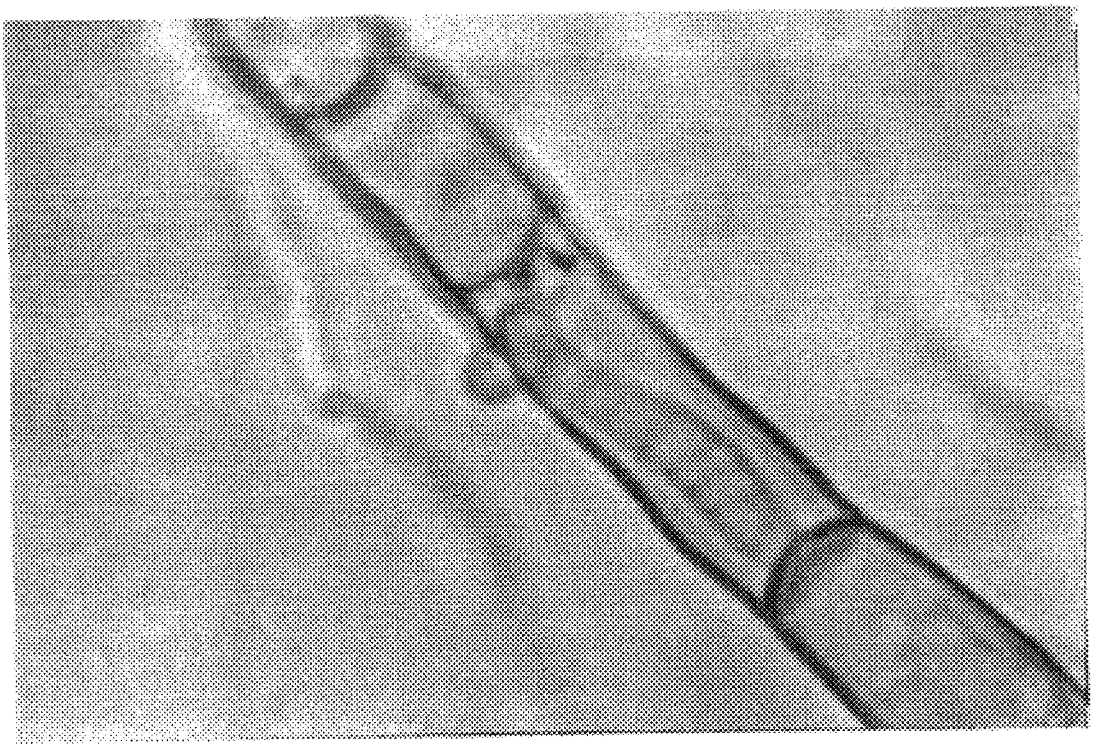
Figure 5A:
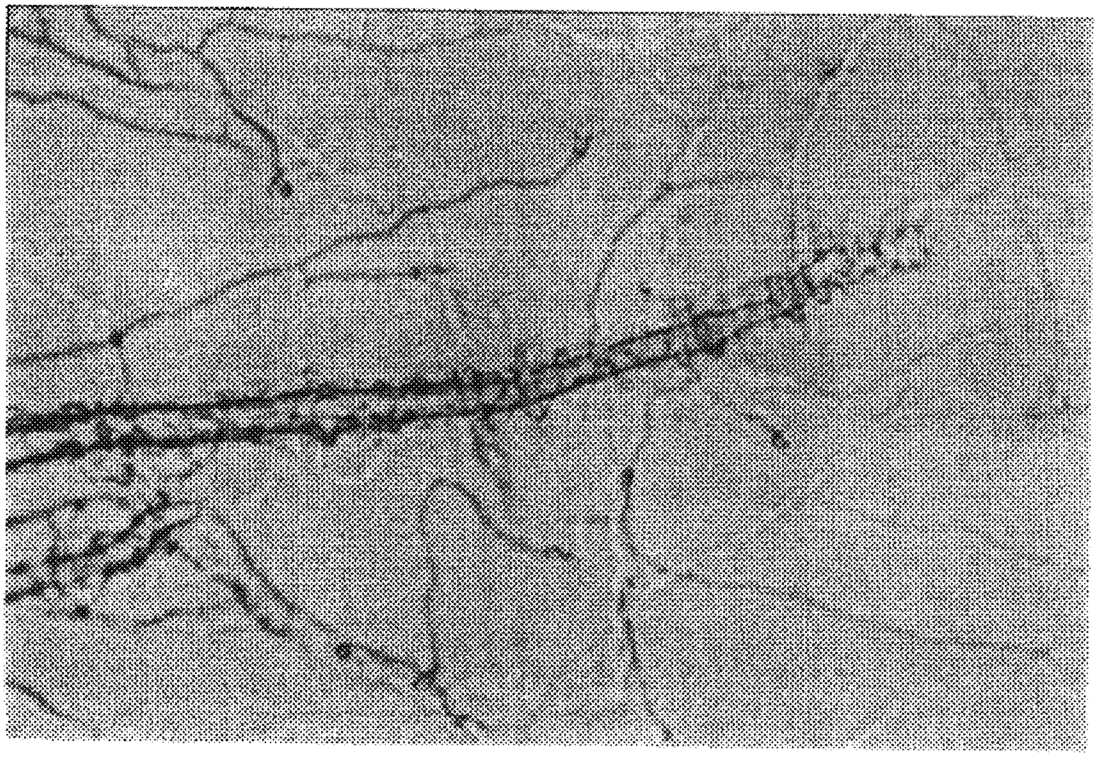
* and FIG. 5A and FIG. 5B illustrate the mycoparasitism of ACM941 at the growth point of the pathogen hyphae (FIG. 5A) and lysis of the pathogen mycelium thereafter (FIG. 5B).
Figure 5B:
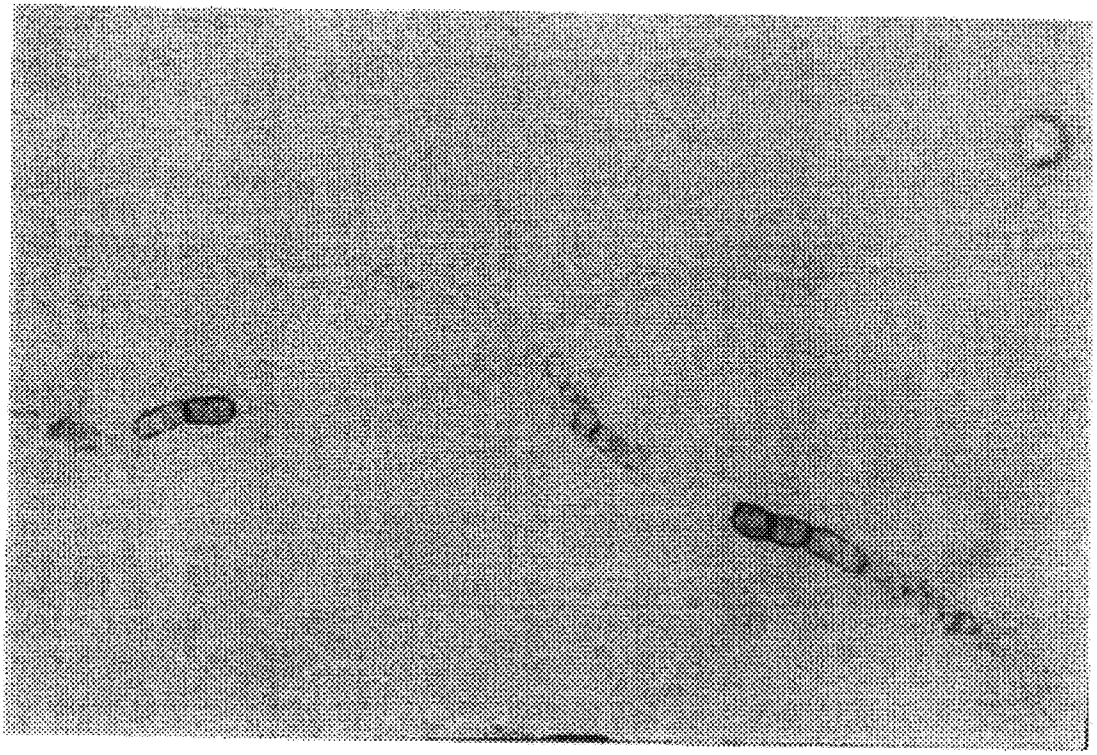

When growing near pathogen hyphae, ACM941 was often stimulated to produce lateral branches that were attracted directly to the pathogen mycelium. Twining, looping and coiling around the mycelium were characteristic responses of ACM941 to neighboring pathogens, as more clearly illustrated in FIG. 3. In most cases, ACM941 appeared to entwine the pathogen mycelium, however, further growth of ACM941 into the encompassed mycelium was not evident. However, penetration and internal growth of hyphae was observed on larger fungi such as *A. alternata* and *R. solani,* as illustrated in FIG. 4A and FIG. 4B. After contact with ACM941, the pathogen mycelium appeared to stop growing, cells became empty due to the loss of cytoplasm and lysis was observed in later stages, as illustrated in FIGS. 5A and 5B.

To summarize, ACM941 was found to destroy pathogen mycelia only after making physical contact. As such, it can be concluded that the antagonistic effect of ACM941 against the pathogens tested was not due to the release of an antibiotic or toxic substance capable of acting at a distance. Accordingly, the mycoparasitic characterization of ACM941 coincided with the results of the greenhouse and field studies reported below.

EXAMPLE 3

Population Proliferation of ACM941 Bioagent in Plant Rhizosphere

Proliferation of ACM941 bioagent in the rhizosphere was examined with six different types of plants including broccoli (*Brassica oleracea* var. italica, cv. Green Sprouting), carnation (*Dianthus caryophyllus,* cv. Grenadin), field pea (*Pisum sativum,* cv. Radley), garden bean (*Phaseolus lunatus,* cv. Tendergreen Improved), tomato (*Lycopersicon esculenium,* cv. Bush Beefsteak) and wheat (*Triticum aestivum,* cv. AC Domain). Seeds were treated with a concentration of $10^7$ spores/mL of ACM941 spore suspension at 5.0 mL/kg seed. Nontreated seeds were used as controls. Seeds were planted in 5-inch plastic pots containing large coarse vermiculite at 2.5 cm deep and one seed per pot. Seeded pots were placed in a growth room operated at 21° C. with a 16 h photoperiod at 350 $mol.m^{-2}.s^{-1}$ light intensity. Seedlings from ACM941 treated and nontreated seeds were removed from their respective pots 7, 21 and 35 days after seeding and shaken with slight agitation of roots to remove as much vermiculite as possible, without fragmenting the root structure. Where present on the day of observation, those plant segments examined included seed coat, primary root 0–3 cm below seed, primary root at 3–6 cm below seed, epicotyl and stem at 0–3 cm above seed, and secondary roots. ACM941 propagula were removed from each segment of individual plants using 0.1% Tween 20 solution and recovered by series dilutions plated on the Gliocladium selective medium developed by Park et al.[20] Colony forming units (CFU) from each plant segment were assessed 6–8 days after inoculation at 20° C. in the dark.

ACM941 bioagent was recovered from all the plant segments of the six different types of plants tested (Table 1). Compared to the amount initially introduced onto the seed coat (0 day after seeding), the bioagent increased 5 to 1463, 240 to 5160, and 112 to 9173 folds at 7, 21 and 35 days after seeding, respectively, ACM941 was also recovered from low stems (epicotyl or hypocotyl) and primary and secondary roots where it was not applied, indicating that the bioagent had grown along with the development of the plants. This rapid increase in the amount of bioagent present in the respective plant tissues observed, was indicative of the potential of the bioagent to provide ongoing protection against pathogenic infection.

TABLE I

Population proliferation of ACM941 bioagent in plant rhizosphere over 35-day period after planting.

| | | Colony forming units (CFU) × 1000 | | | |
|---|---|---|---|---|---|
| Plant | Plant segment | 0 day | 7 day | 21 day | 35 day |
| Garden bean | Seed coat | 17.1 | 824.2 | 4105.0 | 6250.0 |
| (cv. Tendergreen | Hypocotyl/stem (0–3 cm from seed) | —† | 6.0 | 36.2 | 12.5 |
| improved) | Primary root (0–3 cm from seed) | — | 1.4 | 2.7 | 6.5 |
| | Primary root (3–6 cm from seed) | — | 0.3 | 0.8 | 16.4 |
| | Secondary roots | — | 4.4 | 193.9 | 593.9 |
| Broccoli | Seed coat | 0.9 | 53.7 | 284.4 | 101.2 |
| (cv. Green | Hypocotyl/stem (0–3 cm from seed) | — | 6.0 | 65.8 | 41.6 |
| sprouting) | Primary root (0–3 cm from seed) | — | 1.7 | 3.1 | 146.2 |
| | Primary root (3–6 cm from seed) | — | — | 1.7 | 0.7 |
| | Secondary roots | — | — | 49.3 | 54.7 |
| Carnation | Seed coat | 0.4 | 1.9 | 441.7 | 78.3 |
| (cv. Grenadin) | Hypocotyl/stem (0–3 cm from seed) | — | 0.1 | 0.7 | 5.0 |
| | Primary root (0–3 cm from seed) | — | 1.0 | 19.5 | 67.3 |
| | Primary root (3–6 cm from seed) | — | — | 0.7 | 6.2 |
| | Secondary roots | — | — | 12.3 | 10.2 |
| Field pea | Seed coat | 1.2 | 1755.0 | 6191.5 | 11008.3 |
| (cv. Radley) | Epicotyl/stem (0–3 cm from seed) | — | 4.8 | 76.4 | 159.2 |
| | Primary root (0–3 cm from seed) | — | 168.2 | 77.2 | 388.9 |
| | Primary root (3–6 cm from seed) | — | 2.9 | 5.6 | 3.2 |
| | Secondary roots | — | — | 551.0 | 276.9 |
| Tomato | Seed coat | 1.5 | — | — | — |
| (cv. Brush | Hypocotyl/stem (0–3 cm from seed) | — | 1.2 | 11.5 | 10.7 |
| beefsteak) | Primary root (0–3 cm from seed) | — | 3.4 | 1.0 | 6.6 |
| | Primary root (3–6 cm from seed) | — | 0.1 | 0.1 | 1.2 |
| | Secondary roots | — | — | 3.5 | 22.9 |
| Wheat | Seed coat | 3.3 | 46.3 | 3301.1 | 1290.0 |

TABLE I-continued

Population proliferation of ACM941 bioagent in plant rhizosphere over 35-day period after planting.

| Plant | Plant segment | Colony forming units (CFU) × 1000 | | | |
|---|---|---|---|---|---|
| | | 0 day | 7 day | 21 day | 35 day |
| (cv. AC Domain) | Hypocotyl/stem (0–3 cm from seed) | — | 3.4 | 17.1 | 139.4 |
| | Primary root (0–3 cm from seed) | — | 0.8 | 3.2 | 5.3 |
| | Primary root (3–6 cm from seed) | — | 1.1 | 0.2 | 0.4 |
| | Secondary roots | — | 2.9 | 82.4 | 248.3 |

†Plant segment not developed or not found at the time of assessment.

EXAMPLE 4

Effect of Concentration and Timing of Post Seed Treatment on the Efficacy of ACM941 Seed Treatments (1) Effect of Concentrations of ACM941.

Seven concentrations of ACM941 spore suspension ($5\times10^2$, $5\times10^3$, $5\times10^4$, $5\times10^5$, $5\times10^6$, $5\times10^7$, and $1\times10^8$ spores/mL) were evaluated for their effects on emergence and root rot severity when used as seed treatments. The spore suspensions were prepared by washing colonies of 4 week old cultures, grown on PDA medium, followed by series dilutions.

Radley field pea seeds harvested from a diseased field in Morden, Manitoba in 1993 were used in this experiment. The pea seeds were contaminated with Alternaria spp. at 37%, Ascochyta spp. at 5%, Fusarium spp. at 32% and *Rhizocronia solani* at 14%. Seeds were treated with the spore suspensions at 5.0 mL/kg seed. Treated seeds were vigorously shaken after the addition of the suspensions to ensure uniform coverage of the seeds and allowed to air dry before planting. Seeds were planted in wood planting flats (35.5×47.0×9.0 cm) containing soil mixture of 2:1:1 of soil, perlite and peat moss. For each treatment 50 seeds were planted in each of the 4-replicate flats. Planted flats were placed in a growth room maintained at 20° C., with a 14-h photoperiod at 350 $mol.m^{-2}.s^{-1}$ light intensity. Emergence was counted 7 days after planting and root rot severity was rated on a scale of 0 (no visible lesions on lower stem and roots, seedling well developed) to 9 (death of plant, seedling died back quickly after emergence) after digging out plants 14 days after planting. This experiment was conducted at AAFC Research Centre, Morden, Manitoba in 1994.

Seed treatment with ACM941 increased emergence and reduced root rot severity for all concentrations tested compared to the nontreated control (Table 2). The treatment effects were significant when concentrations were equal to or greater than $5\times10^5$ spores/mL. At a concentration of $5\times10^5$ spores/mL, ACM941 increased emergence by 10% and reduced root rot severity by 68%. Concentrations of at least $5\times10^5$ spores/mL were thereafter used in further seed treatment studies.

TABLE 2

Effect of different concentration of ACM941 on the efficacy of seed treatment in field pea.

| Treatment | Emergence (%) | Root rot severity (0–9) |
|---|---|---|
| ACM941, $1\times10^8$ spores/mL | 86.7 ab* | 0.3 d |
| ACM941, $5\times10^7$ spores/mL | 82.0 bc | 0.5 d |
| ACM941, $5\times10^6$ spores/mL | 84.7 ab | 0.8 cd |
| ACM941, $5\times10^5$ spores/mL | 88.0 a | 0.8 cd |
| ACM941, $5\times10^4$ spores/mL | 86.0 ab | 1.6 abc |
| ACM941, $5\times10^3$ spores/mL | 83.3 bc | 1.0 bcd |
| ACM941, $5\times10^2$ spores/mL | 83.3 bc | 1.9 ab |
| Nontreated | 80.0 c | 2.5 a |

*Means in a column followed by the same letter are not significantly different at P = 0.05 (LSD).

(2) Effect of Timing of Post Seed Treatment

The shelf life of ACM941 was examined at 1, 3, 7, 14, 28, and 42 days after seed treatment. Cultivars AC Tamor and Radley field pea seeds harvested from diseased fields in 1995 were used. These seeds were contaminated with Alternaria spp. at 16% and 23%, Ascochyla spp. at 31% and 4%, Fusarium spp. at 22% and 30% and *Rhizoctonia solani* at 13% and 8%, for AC Tamor and Radley, respectively. The seed treatment procedures, and planting and assessment methods used in this experiment were the same as described above. Treated seeds were kept in a 15° C. seed storage room between plantings. This experiment was conducted at AAFC Research Centre, Morden, Manitoba in 1996.

For all the post seed treatment timings examined, seed treatment with ACM941 had greater emergence and lower root rot severity compared to nontreated seeds (Table 3). On AC Tamor, ACM941 increased emergence by 22, 23, 35, 63, 20 and 30%, and reduced root rot severity by 70, 60, 75, 88, 44 and 78% after 1, 3, 7, 14, 29 and 42 days of the seed treatment, respectively. Similarly, on Radley pea, ACM941 increased emergence by 58, 27 and 55%, and reduced root rot severity by 91, 100 and 75% after 1, 3, and 14 days of the seed treatment, respectively. The results indicated that the seed treatment effectiveness was not reduced even after the seeds were treated for 42 days. These results further suggested that the shelf life of ACM941 on treated seeds could be in excess of 42 days.

TABLE 3

Effect of timings of post seed treatment on the efficacy of ACM941 seed treatments in field pea.

| Treatment | AC Tamor Emergence (%) | AC Tamor Root rot severity (0–9) | Radley Emergence (%) | Radley Root rot severity (0–9) |
|---|---|---|---|---|
| Day 1, ACM941 | 84.9 a* | 1.0 b | 95.0 a | 0.1 b |
| Day 1, nontreated | 69.9 b | 3.3 a | 60.0 b | 1.1 a |
| Day 3, ACM941 | 80.0 a | 0.8 b | 69.9 a | 0.0 b |
| Day 3, nontreated | 65.0 b | 2.0 a | 54.9 b | 1.4 a |
| Day 7, ACM941 | 95.0 a | 0.1 a | —† | — |
| Day 7, nontreated | 69.9 b | 0.4 a | — | — |
| Day 14, ACM941 | 90.0 a | 0.1 b | 84.9 a | 0.1 a |
| Day 14 nontreated | 54.9 b | 0.8 a | 54.9 b | 0.4 a |
| Day 28, ACM941 | 90.0 a | 0.5 a | — | — |
| Day 28, nontreated | 75.0 b | 0.9 a | — | — |
| Day 42, ACM941 | 64.5 a | 0.6 b | — | — |
| Day 42, nontreated | 49.5 b | 2.8 a | — | — |

*Data in a column under each seeding date followed by the same letter are not significantly different at P = 0.05 (LSD).
†Data were not collected due to the shortage of seeds.

EXAMPLE 5

Effect of Temperature and Seeding Dates on the Efficacy of ACM941 Seed Treatments (1) Effect of Temperature The efficacy of ACM941 seed treatments were examined at a range of four temperatures (6° C., 10° C., 15° C., and 20° C.) at AAFC Research Centre, Morden, Manitoba in 1994. Temperatures of 6° C., 10° C., and 15° C. were provided in growth cabinets and a temperature of 20° C. was provided in a growth room. All the growth cabinets and the growth room were provided with a 14-h photoperiod at 350 $mol.m^{-2}.s^{-1}$ light intensity. Radley field pea seeds harvested from a diseased field in Morden, Manitoba in 1993 were used. The pea seeds were contaminated with Fusarium spp. at 32%, Alternaria spp. at 37%, Ascochyta spp. at 5% and *Rhizoctonia solani* at 14%. The seed treatment procedures, and planting and assessment methods used in this experiment were the same as described above, Seed treatments with ACM941 increased emergence and reduced root rot severity at all the temperatures tested (Table 4). The seed treatment effects increased with the increase in temperature from 6° C. to 20° C., but not significantly different among the temperatures. At 6° C., ACM941 seed treatment increased emergence by 10%, and reduced root rot severity by 84%. At 20° C., the treatment increased emergence by 24% and reduced root rot severity by 89%. These results indicated that the effectiveness of ACM941 seed treatment was not significantly affected with the change of temperature within the 6–20° C. range, which is the range of soil temperatures at seeding time and during the growing season for cool season crops. These results after suggest that ACM941 can be effectively employed as a seed treatment for cool season crops.

TABLE 4

Effect of temperature on the efficacy of ACM941 seed treatments in field pea.

| Treatment | Emergence (%) | Root rot severity (0–9) |
|---|---|---|
| 6° C., ACM941 | 76.7 a* | 0.5 b |
| 6° C., nontreated | 63.3 b | 2.2 a |

TABLE 4-continued

Effect of temperature on the efficacy of ACM941 seed treatments in field pea.

| Treatment | Emergence (%) | Root rot severity (0–9) |
|---|---|---|
| 10° C., ACM941 | 72.0 a | 0.5 b |
| 10° C., nontreated | 66.7 a | 1.8 a |
| 15° C., ACM941 | 73.3 a | 0.6 b |
| 15° C., nontreated | 66.7 a | 2.8 a |
| 20° C., ACM941 | 86.0 a | 0.3 b |
| 20° C., nontreated | 66.7 b | 2.8 a |

*Data in a column under each temperature followed by the same letter are not significantly different at P = 0.05 (LSD).

(2) Effect of Seeding Dates

Field experiments were conducted at the AAFC Research Centre, Morden, Manitoba in 1995 and 1996 to determine the effect of three seeding dates (early, optimum and late) on the efficacy of ACM941 seed treatments in improving emergence and yield of field crops. Certified seed of cultivar AC Tamor and Radley field pea was used in each testing year. For each seeding date, seeds were treated with ACM941 spore suspensions at $10^7$ spores/mL and a rate of 5.0 mL/kg seed or with Thiram 75 WP (75% thiram) at 1.0 g a.i./kg seed. The experiments were carried out in a split-plot design with seeding dates in the main plots and cultivars and treatments in the subplots on a sandy loam soil in 1995 and a clay loam soil in 1996. The peas were grown in 4-row plots with four replicates per treatment. The plots were 3.0 m long with 30 cm row spacing and 1.2 m apart between plots. The early seeding dates were May 1 and 3, the optimum seeding dates were May 15 and 16, and the late seeding dates were May 29 and 30, for 1995 and 1996, respectively. The seeding rate was 80 seeds per row each year. Standard management practices for Manitoba were followed for weed control and fertilization of the crop. Emergence was counted on each plot 4 weeks after planting. Plants were harvested at maturity and the total seed yield and 1000-seed weight were collected when seeds were air dried to 13% seed moisture content.

On the average of the two cultivars used, seed treatment with ACM941 increased emergence and seed yield for all the seeding dates in the two testing years compared to the nontreated control (Table 5). However, the treatment effects were not observed with cv. Radley when seeded at an optimum date and cv. AC Timor when seeded at a late date in 1996. On the average of the two cultivars and the two testing years, ACM941 increased emergence by 6%, 30% and 7%, and yield by 19%, 47% and 6%, for early, optimum and late seeding dates, respectively. These effects were equal to or greater than those achieved with thiram seed treatments at the various seeding dates. These results suggest that ACM941 is an effective seed treatment for various seeding timings required for cool season crops. Results of this study were also in agreement with previous observations that ACM941 seed treatment was effective in controlling seed and root rot diseases under various temperature conditions.

TABLE 5

Effect of seeding dates on the efficacy of ACM941 seed treatment in field pea in 1995 and 1996.

| | 1995 | | | | 1996 | | | |
|---|---|---|---|---|---|---|---|---|
| | AC Tamor | | Radley | | AC Tamor | | Radley | |
| | Emergence | Yield | Emergence | Yield | Emergence | Yield | Emergence | Yield |
| Early, ACM941 | 70.4 a* | 4548 a | 68.9 a | 4030 a | 64.3 b* | 2706 a | 77.8 a | 1123 a |
| Early, thiram | 66.7 a | 4934 a | 72.4 a | 4566 a | 81.6 a | 2069 b | 79.5 a | 1295 a |
| Early, nontreated | 63.2 a | 3660 b | 64.8 a | 3642 a | 63.8 b | 1924 b | 73.8 a | 648 b |
| Optimum, ACM941 | 65.7 a | 3508 a | 73.5 ab | 2623 ab | 74.5 b | 2995 a | 68.2 b | 1304 a |
| Optimum, thiram | 62.8 a | 3855 a | 81.3 a | 2901 a | 75.5 a | 3152 a | 84.7 a | 1580 a |
| Optimum, | 37.5 b | 2094 b | 47.7 b | 2245 b | 72.2 a | 1689 b | 77.7 a | 1482 a |
| Late, ACM941 | 44.7 a | 3077 a | 48.7 a | 3323 a | 70.5 b | 2685 a | 76.5 a | 1940 a |
| Late, thiram | 35.8 b | 2454 a | 55.0 a | 3235 a | 87.2 a | 2857 a | 84.7 a | 1706 a |
| Late, nontreated | 35.0 b | 2321 b | 55.5 a | 2951 a | 76.3 b | 3291 a | 62.8 b | 1672 a |

*Data in a column under each seeding date, followed by the same letter are not significantly different at P = 0.05 (LSD).

EXAMPLE 6

Comparative Evaluation of ACM941 and Registered Fungicides for the Control of Common Root Rot Pathogens in Field Crops, Vegetables, and Ornamentals (1) Efficacy against *Rhizoctonia solani*

*R. solani* causes rhizoctonia root rot, which is one of the major diseases of pea root rot complex (PRRC) and a major disease of more than 500 genera of plants in the United States[21]. In the present study, ACM941 seed treatment was evaluated for the control of rhizoctonia root rot in four field crops including canola (*Brassica napus*), field bean (*Phaseolus vulgaris*), field pea (*Pisum sativum*) and sugar beet (*Beta vulgaris*), 10 vegetables including table beet (*B. vulgaris* subsp. vulgaris), broccoli (*Brassica oleracea* var. *italica*), brussel sprouts (*Brassica oleracea* var. *gemmifera*), cabbage (*Brassica oleracea* var. *capitata*), cauliflower (*Brassica oleracea* var. *botrytis*), cucumber (*Cucumis sativus*), egg plant (*Solanum melongena*), garden pea (*Pisum sativum*), pepper (*Capsicum annuum*) and tomato (*Lycopersicon esculentum*), and one ornamental, marigold (*Tagetes erecta*) in growth room experiments, and on two varieties of field pea in field trials in 1996–1997. Certified seeds of these varieties obtained from commercial seed companies were used in these experiments. Seeds were treated with ACM941 at $10^7$ spores/mL and 5.0 mL/kg seed. The effectiveness of ACM941 was compared with appropriate fungicides including Vitaflo™ 280 (14.9% carbathiin+13.2% thiram) at 0.93 g a.i./kg seed for canola and field bean and Thiram 75WP (75% thiram) at 1.0 g a.i./kg seed for the remaining crops.

In growth room experiments, seeds were planted in wood planting flats (35.5×47.0×9.0 cm) containing soil mixture of 2:1:1 of soil, perlite and peat moss. The soil mixture was pasteurized and mixed at about 2% v/v with artificially infested vermiculite that was moistened with 0.4% malt extract, autoclaved, inoculated with *B. solani,* and incubated at 20° C. for 7 days prior to the planting. The pathogen isolates used in these experiments were in anastomosis group 2 (AG-2) for cabbage, cauliflower, broccoli and brussel sprouts; and AG-4 for the remaining crops. For each treatment 100 seeds were planted in each of the 4-replicate flats. The planted flats were placed in a growth room maintained at 20° C. and with a 14-h photoperiod at 350 $mol.m^{-2}.s^{-1}$ light intensity by fluorescent and incandescent lamps. All experiments were arranged in a completely randomized block design. Emergence was counted 7 days after planting and other parameters were assessed after digging out plants 14 to 16 days after planting. Disease severity was rated on a scale of 0 (no visible lesions on lower stem and roots, seedling is well developed) to 9 (death of plant, the seedling died back quickly after emergence). The experiments were conducted at AAFC Research Centre, Morden, Manitoba in 1995–1998.

In field experiments, the effectiveness of ACM941 seed treatment was compared with thiram fungicide on two field pea varieties, namely AC Tamor and Radley, at Agriculture and Agri-Food Canada Research Centre, Morden, Manitoba on a clay loam soil in 1996 and a sandy loam soil in 1997. Experiments were carried out in a split-plot design with cultivars in the main plots and treatments in the subplots, having four replicates per treatment. Plots were 3.0 m long having 4 rows with 30 cm row spacing and 1.2 m between plots. The plots were inoculated with artificially infected wheat seeds that were autoclaved, inoculated with *R. solani,* incubated at 20° C. for 3–4 weeks, and air dried. The inoculum was applied to the soil by mixing with pea seeds prior to the seeding and seeded simultaneously at 10 g/row. The seeding rate was 80 seeds per row for both years. Standard management practices for Manitoba were followed for weed control and fertilization of the crop. Emergence was counted on each plot 3 weeks after planting. Plants were harvested at maturity and the total seed yield and 1000-seed weight were collected when seeds were air dried to 13% seed moisture content.

Seeds treated with ACM941 bioagent had greater emergence, fresh and dry weights and lower rhizoctonia root rot severity than the nontreated controls for all 15 crops tested in growth room experiments (Table 6). On average, ACM941 increased emergence by 52%, 142% and 9%, fresh weight by 60%, 8% and 28%, and dry weight by 58%, 5% and 20%, and reduced root disease severity by 44%, 27% and 30%, for field crops, vegetables and ornamentals, respectively. On the average of all 15 crops, ACM941 increased emergence by 109%, fresh weight by 28%, dry weight by 20%, and reduced root disease severity by 30%, compared to the nontreated control. These effects were greater than these achieved with fungicide seed treatments which increased emergence by 105%, fresh weight by 27%, dry weight by 21%, and reduced root disease severity by 24%.

Disease pressure was relatively higher in the field experiments conducted in 1996 than those conducted in 1997 (Table 7). As a result, emergence was generally low for all the treatments and treatment effect was clearly observed in 1996. Compared to the nontreated controls, ACM941 increased emergence by 13% and yield by 16%, on average in the two varieties in 1996. Under the same condition, thiram increased emergence by only 2%, but reduced yield by 12.5%. In 1997, both ACM941 bioagent and thiram fungicide increased emergence significantly. However, these treatments did not increase the yield. The lack of yield advantage of these treatments in 1997 might have been due to the lower disease pressure and high yielding potential of all the treatments and the nontreated controls. Overall, ACM941 increased emergence by 21% and yield by 6% based on the two years of field experiments. These effects were greater than those achieved with commercial fungicide treatments, which increased emergence by 17%, but reduced yield by 10%.

The above results suggest that ACM941 is an effective seed treatment for controlling rhizoctonia root rot on all crops in both a controlled environment and field conditions. The effectiveness was greater or equal to those achieved with commercial fungicides.

(2) Efficacy against *Fusarium solani*

*F. solani* is a major pathogen of PRRC and also causes fusarium root rot of more than 100 genera of plants in the United States.[21] In the present study, ACM941 seed treatment was evaluated for the control of fusarium root rot on Radley field pea in growth room experiments and on AC Tamor and Radley field pea in field experiments in 1996–1997, in comparison with the registered fungicide Thiram 75W. The seed treatment procedures, inoculum preparation, inoculation and assessment methods for both growth room and field experiments were the same as described above.

ACM941 seeds treatments reduced fusarium root rot severity, increased emergence, plant health and productivity in both growth room and field experiments, compared to the nontreated controls. In growth room experiments, ACM941 increased emergence by 165%, fresh weight by 29%, dry weight by 11%, and reduced root disease severity by 32% (Table 8). These effects were greater than but not significantly different from those achieved with the fungicide seed treatment. Under field conditions, ACM941 increased emergence by 7% and 21%, and yield by 6% and 7%, on the average of the two varieties, in 1996 and 1997, respectively (Table 7). Overall, ACM941 increased emergence by 21% and yield by 6% based on the two years of field experiments. These effects were greater than those achieved with the commercial fungicide, which increased emergence by 15%, but reduced yield by 2%. These results indicate that ACM941 is an effective seed treatment for controlling fusarium root rot in both a controlled environment and field conditions. The effectiveness was greater than or equal to those achieved with the commercial fungicide.

TABLE 6

Comparative evaluation ACM941 bioagent and registered fungicides for the control of *Rhizoctonia solani* in growth room experiments.

| Crop/Variety | Treatment | Emergence (%) | Root/foot rot severity (0–9) | Fresh wt. (g/plant) | Dry wt. (g/plant) |
|---|---|---|---|---|---|
| Canola (cv. AC Excel) | ACM941 | 95.0 a* | 1.3 a | 13.0 a | 1.10 a |
| | Vitaflo 280 | 92.5 a | 2.2 a | 12.2 a | 1.15 a |
| | Nontreated | 87.5 a | 2.2 a | 9.0 a | 0.68 a |
| Field bean (cv. Seafarer) | ACM941 | 55.0 ab | 0.5 a | 24.6 a | 2.40 a |
| | Vitaflo 280 | 70.0 a | 0.8 a | 28.8 a | 2.73 a |
| | Nontreated | 50.0 b | 1.7 a | 19.3 a | 1.98 a |
| Field pea (cv. Radley) | ACM941 | 28.8 b | 3.6 a | 2.3 a | 0.26 a |
| | Thiram | 55.6 a | 3.4 a | 2.4 a | 0.27 a |
| | Nontreated | 16.3 c | 3.6 a | 2.2 a | 0.25 a |
| Sugar beet (cv. US H2O) | ACM941 | 42.5 ab | 1.6 b | 4.2 a | 0.27 a |
| | Thiram | 57.5 a | 1.6 b | 4.4 a | 0.29 a |
| | Nontreated | 20.0 b | 4.3 a | 1.6 b | 0.11 b |
| Table beet (cv. Ruby Queen) | ACM941 | 50.8 ab | 2.5 b | 0.1 a | 0.01 a |
| | Thiram | 78.5 a | 2.3 b | 0.1 a | 0.01 a |
| | Nontreated | 22.8 b | 3.1 a | 0.1 a | 0.01 a |
| Broccoli (cv. Green Sprouting) | ACM941 | 31.5 a | 3.7 b | 0.1 a | 0.01 a |
| | Thiram | 34.0 a | 5.1 ab | 0.1 a | 0.01 a |
| | Nontreated | 17.5 b | 6.0 a | 0.1 a | 0.01 a |
| Brussel Sprouts (cv. Long Island) | ACM941 | 29.0 a | 3.1 a | 0.3 a | 0.03 a |
| | Thiram | 19.5 b | 2.8 a | 0.2 ab | 0.02 a |
| | Nontreated | 5.3 c | 3.5 a | 0.2 b | 0.02 a |
| Cabbage (cv. Golden Acre) | ACM941 | 52.3 a | 2.6 b | 0.2 a | 0.01 a |
| | Thiram | 59.5 a | 2.9 b | 0.2 a | 0.01 a |
| | Nontreated | 25.3 b | 4.7 a | 0.1 a | 0.01 a |
| Cauliflower, (cv. Early Snowball) | ACM941 | 26.5 a | 3.3 a | 0.1 a | 0.01 a |
| | Thiram | 11.5 b | 4.0 a | 0.1 a | 0.01 a |
| | Nontreated | 6.3 b | 4.9 a | 0.1 a | 0.01 a |

TABLE 6-continued

Comparative evaluation ACM941 bioagent and registered fungicides for the control of *Rhizoctonia solani* in growth room experiments.

| Crop/Variety | Treatment | Emergence (%) | Root/foot rot severity (0–9) | Fresh wt. (g/plant) | Dry wt. (g/plant) |
|---|---|---|---|---|---|
| Cucumber, (cv. Imp. Long Green) | ACM941 | 65.8 a | 2.2 b | 0.5 a | 0.05 a |
| | Thiram | 49.0 b | 2.2 b | 0.5 a | 0.06 a |
| | Nontreated | 19.5 c | 4.9 a | 0.4 b | 0.05 a |
| Egg Plant (cv. Early Long Purple) | ACM941 | 77.0 a | 1.7 a | 0.1 a | 0.01 a |
| | Thiram | 79.3 a | 1.9 a | 0.1 a | 0.01 a |
| | Nontreated | 43.5 b | 2.1 a | 0.1 a | 0.01 a |
| Garden Pea (cv. Green Arrow) | ACM941 | 89.8 a | 1.8 b | 1.3 a | 0.15 a |
| | Thiram | 89.2 a | 2.1 b | 1.3 a | 0.15 a |
| | Nontreated | 82.8 b | 3.4 a | 1.2 b | 0.15 a |
| Pepper (cv. California Wonder) | ACM941 | 82.0 a | 1.4 a | 0.1 a | 0.01 a |
| | Thiram | 70.5 b | 1.3 a | 0.1 a | 0.01 a |
| | Nontreated | 73.2 ab | 1.4 a | 0.1 a | 0.01 a |
| Tomato (cv. Bush Beefsteak) | ACM941 | 84.5 a | 1.5 a | 0.1 a | 0.01 a |
| | Thiram | 87.8 a | 1.5 a | 0.1 a | 0.01 a |
| | Nontreated | 77.2 b | 1.6 a | 0.1 a | 0.01 a |
| Marigold (cv. Lemondrop) | ACM941 | 68.5 ab | 2.2 a | 0.5 a | 0.06 a |
| | Thiram | 75.2 a | 2.1 a | 0.5 a | 0.06 a |
| | Nontreated | 63.0 b | 2.1 a | 0.5 a | 0.05 a |

*Data in a column under each crop/cultivar followed by the same letter are not significantly different at P = 0.05 (LSD).

TABLE 7

Comparative evaluation ACM941 bioagent and thiram fungicide for the control of *Rhizoctonia solani*, *Fusarium solani*, *Fusarium oxysporium*, *Mycosphaerella pinodes* and *Sclerotinia sclerotiorum* under field conditions in 1996 and 1997.

| | AC Tamor | | Radley | | AC Tamor | | Radley | |
|---|---|---|---|---|---|---|---|---|
| | Emergence | Yield | Emergence | Yield | Emergence | Yield | Emergence | Yield |
| | | | | *Rhizoctonia solani* | | | | |
| ACM941 | 49.8 a* | 3035 a | 53.9 a | 2269 a | 66.6 b | 5183 a | 65.5 a | 5103 a |
| Thiram | 45.5 a | 2497 a | 47.4 a | 1589 a | 76.0 a | 5367 a | 58.6 b | 4666 a |
| Nontreated | 43.5 a | 2930 a | 48.0 a | 1769 a | 50.4 c | 5609 a | 51.8 c | 5183 a |
| | | | | *Fusarium solani* | | | | |
| ACM941 | 67.0 a | 6009 a | 77.6 a | 3356 a | 66.1 a | 5881 a | 74.8 a | 3656 a |
| Thiram | 76.1 a | 5374 a | 81.4 a | 3674 a | 66.2 a | 5600 a | 65.7 b | 3379 a |
| Nontreated | 64.9 a | 5411 a | 70.4 a | 3326 a | 54.5 b | 5235 a | 61.6 b | 3641 a |
| | | | | *Fusarium oxysporium* | | | | |
| ACM941 | 72.0 ab | 5446 a | 89.1 a | 3050 a | 57.2 b | 6035 a | 76.7 a | 6037 a |
| Thiram | 78.3 a | 5203 a | 85.9 ab | 2442 a | 84.0 a | 6625 a | 63.8 ab | 5037 b |
| Nontreated | 66.6 b | 5232 a | 79.1 b | 2099 a | 47.3 c | 6094 a | 55.3 b | 5345 b |
| | | | | *Mycosphaerella pinodes* | | | | |
| ACM941 | 70.8 a | 2595 a | 78.5 ab | 1661 a | 72.1 a | 5201 ab | 80.1 a | 3672 a |
| Thiram | 76.3 a | 2140 ab | 84.5 a | 1623 a | 80.0 a | 5645 a | 80.2 a | 3328 a |
| Nontreated | 69.8 a | 1375 b | 70.6 b | 1528 a | 71.0 a | 4896 b | 73.4 a | 3456 a |
| | | | | *Sclerotinia Sclerotiorum* | | | | |
| ACM941 | 37.9 ab | 4989 a | 41.4 ab | 2954 a | 41.8 a | 6640 a | 53.0 a | 4973 a |
| Thiram | 41.8 a | 4327 a | 48.9 a | 2598 a | 49.7 a | 5402 b | 50.5 a | 5049 a |
| Nontreated | 29.8 b | 4225 a | 34.3 b | 2499 a | 37.1 a | 5227 b | 40.2 b | 4398 b |

*Data in a column under each pathogen followed by the same letter are not significantly different at P = 0.05 (LSD).

(3) Efficacy against *Fusarium oxysporium*

*F. oxysporium* is also a major pathogen of PRRC and causes wilt diseases in more than 150 genera of plants including field and horticultural crops, vegetables and ornamentals in the United States.[21] In the present study, ACM941 seed treatment was evaluated for the control of fusarium wilt on Radley field pea in growth room experiments and on AC Tamor and Radley field pea in field experiments in 1996–1997, in comparison with the registered fungicide Thiram 75W. The seed treatment procedures, inoculum preparation, inoculation and assessment methods for both growth room and field experiments were the same as described above.

ACM941 seed treatments reduced fusarium root rot severity, increased emergence, plant health and productivity in both growth room and field experiments, compared to the nontreated controls. In growth room experiments, ACM941 increased emergence by 117%, fresh weight by 9%, dry weight by 12%, and reduced wilt disease severity by 19% (Table 8). These effects were less but not significantly different from those achieved with the fungicide seed treatment. Under field conditions, ACM94 1 increased emergence by 10% and 30%, and yield by 25% and 6%, on the average of the two varieties, in 1996 and 1997, respectively (Table 7). Overall, ACM941 increased emergence by 20% and yield by 15%. These effects were equal to or greater than those achieved with the commercial fungicide, which increased emergence by 30% and yield by 5%. These results indicate that ACM941 is an effective seed treatment for controlling fusarium root rot in both a controlled environment and field conditions. Overall, comparison of ACM941 with the fungicide showed that seed treatment with ACM941 had a relatively lower emergence but a greater yield increase. These results reflect the mode of actions of the ACM941 bioagent, which kill pathogens by mycoparasitism and protects plants from future pathogen infection by colonizing the plant rhizosphere, as illustrated in previous examples.

(4) Efficacy against *Mycosphaerella pinodes*

*M. pinodes* is the causal agent of mycosphaerella blight, which is the most important disease of field pea in the world. In addition, *M. pinodes* causes foliar disease and root rot in six genera of pulse crops in the United States.[21] In the present study, ACM941 seed treatment was evaluated for the control of mycosphaerella seedling blight/root rot on Radley field pea in growth room experiments and on AC Tamor and Radley field pea in field experiments in 1996–1997, in comparison with the registered fungicide Thiram 75W. The seed treatment procedures, inoculum preparation, inoculation and assessment methods for both growth room and field experiments were the same as described above.

ACM941 seed treatments reduced mycosphaerella seedling blight/root rot severity, increased emergence, plant health and productivity in both growth room and field experiments, compared to the nontreated controls. In growth room experiments, ACM941 increased emergence by 56%, fresh weight by 4%, dry weight by 11%, and reduced root disease severity by 34% (Table 8). These effects were greater than but not significantly different from those achieved with the fungicide seed treatment.

Under field conditions, ACM941 increased emergence by 6% and 5%, and yield by 48% and 6%, on the average of the two varieties, in 1996 and 1997, respectively (Table 7). Overall, ACM941 increased emergence by 6% and yield by 28%. These effects were equal to or greater than those achieved with the commercial fungicide, which increased emergence by 13% and yield by 18%. These results indicate that ACM941 is an effective seed treatment for controlling mycosphaerella seedling blight/root rot in both a controlled environment and field conditions. The greater yield improvement of ACM941 relative to the commercial fungicide coincided with the results reported above and further verified the mode of actions of ACM941 bioagent against pathogens, as illustrated in previous examples.

(5) Efficacy against *Sclerotinia sclerotiorum*

*S. sclerotiorum* causes white mold or sclerotinia rot, which is an economically important disease on more than 177 genera of plants in the United States.[21] In the present study ACM941 seed treatment was evaluated for the control of sclerotinia rot on Radley field pea in growth room experiments and on AC Tamor and Radley field pea in field experiments in 1996–1997. in comparison with the registered fungicide Thiram 75W. The seed treatment procedures, inoculum preparation, inoculation and assessment methods for both growth room and field experiments were the same as described above.

ACM941 seed treatments reduced sclerotinia rot severity, increased emergence, plant health and productivity in both growth room and field experiments, compared to the nontreated controls. In greenhouse experiments, ACM941 increased emergence by 87%, fresh weight by 14%, and reduced root disease severity by 24% (Table 8). These effects were equal to or greater than those achieved with the fungicide seed treatment. Neither ACM941 nor thiram fungicide showed an increase in dry weight compared to the nontreated control, Under field conditions, ACM941 increased emergence by 24% and 22%, and yield by 18% and 20%, on the average of the two varieties, in 1996 and 1997, respectively (Table 7). Overall, ACM941 increased emergence by 23% and yield by 19%. These effects were equal to or greater than those achieved with the commercial fungicide, which increased emergence by 36% and yield by 6%. These results indicate that ACM941 is an effective seed treatment for controlling sclerotina rot in both a controlled environment and field conditions. Once again, the greater yield improvement of ACM941 relative to the commercial fungicide coincided with the results reported above and further verified the mode of actions of ACM941 bioagent against pathogens, as illustrated in previous examples.

TABLE 8

Comparative evaluation ACM941 bioagent and registered fungicides for the control of *Fusarium graminearum*, *Fusarium solani*, *Fusarium oxysporum*, *Mycosphaerella pinodes*, *Sclerotinia sclerotiorum* and *Bipolaris sorokiniana* in growth room experiments.

| Crop/variety | Treatment | Emergence (%) | Root rot severity (0–9) | Fresh wt. (g/plant) | Dry wt. (g/plant) |
|---|---|---|---|---|---|
| | | *Fusarium solani* | | | |
| Field pea (cv. Radley) | ACM941 | 61.3 a | 3.0 b | 2.7 a | 0.31 a |
| | Thiram | 57.5 a | 3.3 ab | 2.7 a | 0.27 a |
| | Nontreated | 23.1 b | 4.4 a | 2.1 b | 0.28 a |
| | | *Fusarium oxysporum* | | | |
| Field pea (cv. Radley) | ACM941 | 47.5 b* | 2.1 a | 2.4 a | 0.29 a |
| | Thiram | 86.3 a | 1.3 a | 3.1 a | 0.34 a |
| | Nontreated | 21.9 c | 2.6 a | 2.2 a | 0.26 a |
| | | *Mycosphaerella Pinodes* | | | |
| Field pea (cv. Radley) | ACM941 | 76.3 a | 2.1 a | 2.1 a | 0.31 a |
| | Thiram | 67.5 a | 2.3 a | 3.1 a | 0.32 a |
| | Nontreated | 48.8 b | 3.2 a | 2.6 a | 0.28 b |

TABLE 8-continued

Comparative evaluation ACM941 bioagent and registered fungicides for the control of *Fusarium graminearum*, *Fusarium solani*, *Fusarium oxysporum*, *Mycosphaerella pinodes*, *Sclerotinia sclerotiorum* and *Bipolaris sorokiniana* in growth room experiments.

| Crop/variety | Treatment | Emergence (%) | Root rot severity (0–9) | Fresh wt. (g/plant) | Dry wt. (g/plant) |
|---|---|---|---|---|---|
| | | *Sclerotinia Sclerotiorum* | | | |
| Field pea (cv. Radley) | ACM941 | 45.6 b | 2.9 b | 2.4 a | 0.25 a |
| | Thiram | 68.1 a | 3.2 ab | 2.2 a | 0.23 a |
| | Nontreated | 24.4 c | 3.8 a | 2.1 a | 0.26 a |
| | | *Fusarium graminearum* | | | |
| Wheat (cv. Sceptre) | ACM941 | 77.5 a | 0.5 b | 7.9 a | 1.25 a |
| | Vitaflo 280 | 60.0 a | 2.1 a | 4.32 b | 0.75 b |
| | nontreated | 67.5 a | 1.3 ab | 4.85 b | 0.82 b |
| Barley (cv. Harrington) | ACM941 | 90.0 a | 1.5 ab | 6.7 a | 0.95 a |
| | Vitaflo 280 | 85.0 a | 1.3 b | 6.68 a | 1.08 a |
| | nontreated | 90.0 a | 2.4 a | 6.50 a | 1.00 a |
| | | *Bipolaris sorokiniana* | | | |
| Wheat (cv. Sceptre) | ACM941 | 32.5 ab* | 0.6 ab | 1.8 b | 0.48 b |
| | Vitaflo 280 | 55.0 a | 0.4 b | 3.0 a | 0.45 a |
| | nontreated | 20.0 b | 0.8 a | 0.8 b | 0.14 b |
| Barley (cv. Harrington) | ACM941 | 72.5 a | 0.6 b | 10.2 a | 1.05 a |
| | Vitaflo 280 | 82.5 a | 0.5 b | 10.0 a | 1.00 a |
| | nontreated | 75.0 a | 0.7 a | 9.0 b | 0.80 b |

*Data in a column under each cultivar followed by the same letter are not significantly different at P = 0.05 (LSD).

(6) Efficacy against *Fusarium graminearum*

*F. graminearum* causes fusarium head blight of wheat and barley, which is the most damaging disease of these crops in the world. In addition, the pathogen causes head blight and root rot on more than 20 genera of plants in the United States.[21] In the present study, ACM941 seed treatment was evaluated for the control of seedling blight and root rot on Scepter wheat and Harrington barley in growth room experiments and in field experiments in 1996–1997, in comparison with the registered fungicide Vitaflo-280 (14.9% carbathiin+13.2% thiram). The seed treatment procedures, inoculum preparation, inoculation and assessment methods for both growth room and field experiments were the same as described above.

ACM941 seed treatments, in general, reduced fusarium seedling blight/root rot severity, increased emergence, plant health and productivity in both growth room and field experiments, compared to the nontreated controls. In growth room experiments, ACM941 increased emergence by 7%, fresh weight by 33%, dry weight by 26%, and reduced root disease severity by 50%, on the average of the two crops (Table 8). These effects were greater than but not significantly different from those achieved with the fungicide seed treatment. Under field conditions, ACM941 did not show an effect on emergence but increased yield by 1% each year on the average of the two varieties (Table 9), These effects were less but not significantly different from those achieved with the commercial fungicide, which increased emergence by 5% and yield by 3%. The lack of seed treatment effect was attributed to the low disease pressure and high yield potential of these crops in the two years of field experiments.

(7) Efficacy against *Bipolaris sorokiniana*

*B. sorokiniana* is the causal agent of common root rot of wheat and barley, which is an economically important disease of these crops throughout the world. In addition, the pathogen causes leaf blotch and root rot on more than 40 genera of plants in the United States.[21] In the present study, ACM941 seed treatment was evaluated for the control of common root rot on Sceptre wheat and Harrington barley in growth room experiments and in field experiments in 1996–1997, in comparison with the registered fungicide Vitaflo-280 (14.9% carbathiin+13.2% thiram). The seed treatment procedures, inoculum preparation, inoculation and assessment methods for both growth room and field experiments were the same as described above.

ACM941 seed treatments reduced common root rot severity, increased emergence, plant health and productivity in both growth room and field experiments, compared to the nontreated controls. In growth room experiments, ACM941 increased emergence by 30%, fresh weight by 69%, dry weight by 137%, and reduced root disease severity by 20%, on the average of the two crops (Table 8). These effects were equal to or greater than those achieved with the fungicide seed treatment. Under field conditions, ACM941 increased emergence by 4% in 1996 and 11% in 1997, on the average of the two crops. Neither ACM941 nor Vitaflo-280 fungicide illustrated a yield incrase in 1997, but increased yield by 13% and 19% by the respective treatments in 1996 (Table 9). Overall, ACM941 increased emergence by 8% and yield by 4%. These effects were less but not significantly different from those achieved with the commercial fungicide, which increased emergence by 13% and yield by 7%. These results indicate that ACM941 is an effective seed treatment for controlling common root rot caused by *B. sorokiniana* in both a controlled environment and field conditions.

TABLE 9

Comparative evaluation ACM41 bioagent and Vitaflo 280 fungicide for the control of *Fusarium graminearum* and *Bipolaris sorokiniana* under field conditions in 1996 and 1997.

| | 1996 | | | | 1997 | | | |
|---|---|---|---|---|---|---|---|---|
| | Wheat | | Barley | | Wheat | | Barley | |
| | Emergence | Yield | Emergence | Yield | Emergence | Yield | Emergence | Yield |
| | *Fusarium graminearum* | | | | | | | |
| ACM941 | 37.6 b* | 5188 a | 54.9 a | 8290 a | 36.6 a | 2675 a | 55.0 a | 2583 a |
| Vitaflo | 46.9 a | 5468 a | 56.5 a | 7545 a | 38.6 a | 2524 a | 52.9 a | 3128 a |
| Nontreated | 40.7 b | 5599 a | 56.9 a | 7658 a | 36.2 a | 2453 a | 52.6 a | 2799 a |
| | *Bipolaris sorokiniana* | | | | | | | |
| ACM941 | 33.6 a* | 4455 ab | 51.8 a | 8348 a | 38.3 a | 2658 a | 55.6 a | 2685 a |
| Vitaflo | 39.6 a | 4956 a | 55.0 a | 8174 a | 38.2 a | 2926 a | 54.4 a | 2482 a |
| Nontreated | 32.8 a | 3863 b | 48.9 a | 7510 a | 34.5 a | 2884 a | 49.7 b | 2724 a |

*Data in a column under each crop in each year followed by the same letter are not significantly different at P = 0.05 (LSD).

(8) Efficacy against *Pythium ultimum*

*P. ultimum* is a major pathogen of PRRC and a causal agent of seed decay and root rot on a number of plants in the world. In the United States, *P. ultimum* was recorded as being pathogenic to more than 100 genera of plants.[21] In the present study, ACM941 seed treatment was evaluated for the control of pythium root rot on Carneval and Radley field pea in field experiments conducted in 1998 and 1999, in comparison with the registered fungicide Apron FL (31.7% metalaxyl) at 0.36 g a.i./kg seed. The seed treatment procedures, inoculum preparation, inoculation and assessment methods used were the same as described above.

ACM941 seed treatments did not show an effect in emergence in 1998 but increased emergence by 4% in 1999 and increased yield by 3% in 1998 and by 22% in 1999, on the average of the two varieties used (Table 10). Overall, ACM941 increased emergence by 2% and yield by 13%, compared to the nontreated controls. These effects were less but not significantly different from those achieved with the commercial fungicide, which increased emergence by 14% and yield by 16%.

(9) Efficacy against *Aphanomyces euteiches*

*A. euteiches* is one of the most important pathogens of PRRC and causal agent of aphanomyces root rot, which is the most damaging root disease of pulse crops in the world. In addition, the fungus was pathogenic to more than 10 genera of plants in the United States.[21] In the present study, ACM941 seed treatment was evaluated for the control of aphanomyces root rot on Carneval and Radley field pea in field experiments conducted in 1998 and 1999, in comparison with the registered fungicide Thiram 75W. The seed treatment procedures, inoculum preparation, inoculation and assessment methods used were the same as described above.

ACM941 seed treatments increased emergence by 4% in 1999 and yield by 2% in 1998 and 12% in 1999, on the average of the two varieties used (Table 10). Neither ACM941 nor the commercial fungicide showed an effect on emergence in 1998. This lack of treatment effect was likely due to the high emergence rates in 1998. Overall, ACM941 increased emergence by 1% and yield by 7%, compared to the nontreated controls, These effects were less but not significantly different from those achieved with the commercial fungicide, which increased emergence by 11% and yield by 9%.

TABLE 10

Comparative evaluation of ACM941 bioagent and registered fungicides for the control of *Pythium ultimum* and *Aphanomyces euteiches* under field conditions in 1998 and 1999.

| | 1998 | | | | 1999 | | | |
|---|---|---|---|---|---|---|---|---|
| | Carneval | | Radley | | Carneval | | Radley | |
| | Emergence | Yield | Emergence | Yield | Emergence | Yield | Emergence | Yield |
| | *Pythium ultimum* | | | | | | | |
| ACM941 | 83.2 a* | 6313 a | 92.2 a | 5101 a | 82.7 b | 4956 a | 66.2 b | 4201 a |
| Apron | 88.0 a | 6302 a | 96.5 a | 5290 a | 91.1 a | 5343 a | 85.7 a | 4303 a |
| Nontreated | 85.8 a | 6134 a | 92.8 a | 4929 a | 77.7 c | 4131 b | 64.8 b | 3380 b |
| | *Aphanomyces euteiches* | | | | | | | |
| ACM941 | 86.0 a | 6243 a | 93.3 a | 4960 a | 78.0 b | 4970 a | 65.2 ab | 4038 a |
| Thiram | 88.1 a | 6122 a | 91.9 a | 5110 a | 90.3 a | 4986 a | 81.0 a | 4315 a |
| Nontreated | 89.1 a | 6085 a | 95.2 a | 4921 a | 78.6 b | 4212 b | 60.4 b | 3807 b |

*Data in a column under each pathogen followed by the same letter are not significantly different at P = 0.05 (LSD).

EXAMPLE 7

Comparative Evaluation of ACM941 and Registered Fungicides for the Control of Seed borne Fungal Pathogens in Field Crops (1) Efficacy against Seed-borne Fungal Pathogens in Field Pea The effect of ACM941 seed treatment on the recovery of seed-borne fungal pathogens was evaluated using contaminated seeds of AC Tamor and Radley field peas. The seeds were harvested in 1993 from fields that were severely affected by mycosphaerella blight, moderately affected by powdery mildew and fusarium wilt. Seeds were treated with ACM941 at $10^7$ spores/mL and 5.0 mL/kg seed. The effectiveness of ACM941 seed treatment was compared with appropriate fungicides including Captan 50WP (50% captan) at 0.5 g a.i./kg seed or Thiram 75WP (75% thiram) at 1.0 g a.i./kg seed. Treated seeds were plated on potato dextrose agar and incubated at 20° C. with a 14-h photoperiod at 350 mol.m$^{-2}$.s$^{-1}$ light intensity for 14 days. Fungi recovered from the seeds were identified by microscopic examination after this period.

Seed treatment with ACM941 reduced all fungal pathogens recovered from the infested seeds (Table 11). Specifically, ACM941 reduced the recovery of Fusarium spp. by 75% on the average of the two cultivars used, compared to the nontreated controls. This effect was significantly greater than captan fungicide, which had no visible effect on Fusarium spp. and thiram fungicide, which reduced the pathogen by only 2%.

ACM941 reduced the recovery of Alternaria spp. by 73% on the average of the two cultivars used (Table 11). This effect was equal to or greater than the two fungicides, which reduced the pathogen by 49% and 74%, for captan and thiram, respectively.

Similarly, ACM941 reduced the recovery of Ascochyta spp. by 84%, Rhizopus sp. by 71%, and *Rhizoctonia solani* by 100% on the average of the two cultivars used, compared to the nontreated controls (Table 11). These effects were greater than captan fungicide, which reduced the respective pathogens by 31%, 69% and 53%, and thiram fungicide, which reduced the respective pathogens by 40%, 69% and 91%.

The above results suggest that when used as seed treatment, ACM941 has a great potential in controlling most or all seed-borne fungal pathogens that may cause seed decay and root rots in crops. These findings coincide with the results of previous examples of ACM941 seed treatments in both controlled environments and field conditions.

(2) Efficacy against Seed-borne Phase of Fusarium Head Blight and Common Root Rot in Cereals Seed-borne phase of fusarium head blight and common root rot are economically important diseases of cereals throughout the world. In the present study, the effectiveness of ACM941 seed treatment in the control of these diseases was compared with commercial fungicides. The experiments were carried out in a controlled environment using naturally infected seeds of two cultivars of barley (Argyle and Manley) and three cultivars of wheat (Karepwa, Sceptre and Plenty) in the winters 1995 and 1996. Infected seeds of these crops were obtained from fields that were severely affected by fusarium head blight and moderately affected by spot blotch in 1994. Seed infection of Argyle barley was 72%, 16%, 2%, 98%, and 4%, and for Manley barley was 20%, 98%, 2%, 36%, and 8%, by *Fusarium graminearum, Bipolaris sorokiniana, F. avenaceum, Alternaria alternata,* and other Fusarium species, respectively. Seed infection of Katepwa wheat was 70%, 10%, and 30%, for Sceptre wheat was 68%, 29%, and 21%, and for Plenty wheat was 40%, 8%, and 50% by Fusarium spp., *B. sorokiniana,* and *A. alternata,* respectively. The seed-borne infection of these pathogens was determined approximately 3 months after harvest, by sampling 200 seeds of each cultivar and plating on potato dextrose agar (FDA) medium amended with 1 $\mu$g mL$^{-1}$ streptomycin sulfate. Pathogens growing from the seeds were identified by microscopic examination. Seeds were treated with a ACM941 spore suspension of $10^7$ spores/mL at 5.0 mL/kg seed or Thiram 75WP at 1.0 g a.i./kg seed. Treated seeds were planted in wood planting flats (35.5×47.0×9.0 cm) containing soil mixture of 2:1:1 of soil, perlite and peat moss. For each cultivaricrop, 100 seeds were planted in each of the 4-replicate flats for each treatment. The planted flats were placed in a growth cabinet maintained at 20° C., with a 14-h photoperiod at 350 mol.m$^{-2}$.s$^{-1}$ light intensity by fluorescent and incandescent lamps. Emergence was counted 7 days after planting and other parameters were assessed after digging out plants 14 days after planting. Disease severity was rated using the 0–9 scale described above.

In wheat seed treatment, ACM941 increased emergence 63%, fresh weight by 18%, dry weight by 7%, and reduced root disease incidence by 85% and severity by 85%, on the average of the three cultivars (Table 12). These effects were greater than but not significantly different from those achieved with the fungicide seed treatment, which increased emergence by 55%, fresh weight by 25% and dry weight by 15%, and reduced root rot incidence by 61% and severity by 57%.

In the treatment of barley seed, neither ACM941 nor the fungicide increased the emergence, fresh weight or dry

TABLE 11

Effect of ACM941 seed treatment on the recovery of seed-borne fungal pathogens in field pea.

| | | % recovery | | | | |
|---|---|---|---|---|---|---|
| Cultivar | Treatment | Fusarium spp. | *Alternaria alternata* | Ascochyta spp. | Rhizopus sp. | *Rhizoctonia solani* |
| AC | ACM941 | 10.0 b* | 1.1 b | 0.0 a | 8.9 b | 0.0 a |
| | Captan | 40.8 a | 10.6 b | 3.4 a | 8.0 b | 0.7 a |
| | Thiram | 27.8 ab | 11.1 b | 3.3 a | 7.8 b | 0.0 a |
| | Nontreated | 33.3 a | 46.7 a | 5.6 a | 25.6 a | 2.2 a |
| Radley | ACM941 | 6.7 b | 19.1 bc | 1.6 a | 3.8 b | 0.0 c |
| | Captan | 38.4 a | 29.2 ab | 3.8 a | 4.9 b | 8.9 ab |
| | Thiram | 35.9 a | 10.3 c | 3.0 a | 5.1 b | 2.5 bc |
| | Nontreated | 31.9 a | 37.1 a | 4.9 a | 16.0 a | 14.1 a |

*Data in a column under the same cultivar followed by the same letter are not significantly different at P = 0.05 (LSD).

weight (Table 12). Both treatments, however, reduced root rot incidence and severity compared to the nontreated controls. On average of the two cultivars used, ACM941 reduced root rot incidence by 44% and severity by 51%. These effects were greater than those achieved with thiram, which reduced the root rot incidence by 31% and severity by 38%.

Results of this study indicate that seed treatment with ACM941 or fungicides is essential in preserving the potential viability of these infected seeds and that ACM941 has a greater or at least equal power in reducing the harmful effect of seed-borne fungal pathogens on subsequent crops in cereals.

treated with ACM941 bioagent spore suspension at $10^7$ spores/mL at a rate of 5.0 mL/kg seed or with thiram 75WP fungicide at 1.0 g a.i./kg seed. The seed treatment procedures, crop management and assessment methods used in these field experiments were the same as described in previous examples.

All HL seeds had higher emergence than did that of VP seeds for both cultivars in both 1995 and 1996 (Table 13), indicating that the high level of seed-borne infection by *M. pinodes* is responsible for the lower emergence. Seed treatments with ACM941 or thiram increased emergence of both HL and VP seeds in the two testing years. On average of the two cultivars, ACM941 increased emergence of HL seeds by

TABLE 12

Comparative evaluation ACM941 bioagent and thiram fungicide for the control of seed-borne phase of fusarium head blight and common root rot in wheat and barley in growth room experiments.

| Crop | Cultivar | Treatment | Emergence (%) | Root rot incidence (%) | Root rot severity (0–9) | Fresh wt. (g/plant) | Dry wt. (g/plant) |
|---|---|---|---|---|---|---|---|
| Wheat | Katepwa | ACM941 | 76.2 a | 3.5 b | 0.1 b | 1.00 a | 0.21 a |
| | | Thiram | 70.7 a | 12.5 ab | 0.7 ab | 0.96 a | 0.23 a |
| | | Nontreated | 53.7 b | 28.8 a | 1.5 a | 0.60 a | 0.15 a |
| | Sceptre | ACM941 | 55.8 a | 14.6 b | 0.8 b | 0.51 a | 0.11 a |
| | | Thiram | 52.4 a | 24.7 b | 1.1 b | 0.65 a | 0.14 a |
| | | Nontreated | 23.1 b | 85.6 a | 3.9 a | 0.53 a | 0.12 a |
| | Plenty | ACM941 | 87.8 a | 3.8 b | 0.2 c | 0.79 a | 0.19 a |
| | | Thiram | 88.4 a | 10.1 b | 0.6 b | 0.79 a | 0.16 a |
| | | Nontreated | 83.0 a | 22.2 a | 1.1 a | 0.87 a | 0.21 a |
| Barley | Argyle | ACM941 | 93.2 a | 5.9 b | 0.4 b | 1.10 a | 0.27 a |
| | | Thiram | 93.9 a | 10.8 b | 0.5 b | 1.24 a | 0.32 a |
| | | Nontreated | 89.8 a | 22.2 a | 1.4 a | 1.33 a | 0.32 a |
| | Manley | ACM941 | 80.3 a | 75.1 a | 3.3 b | 0.94 a | 0.21 a |
| | | Thiram | 84.3 a | 77.8 a | 4.2 ab | 1.04 a | 0.22 a |
| | | Nontreated | 85.7 a | 87.2 a | 4.8 a | 0.98 a | 0.28 a |

*Data in a column under each cultivar followed by the same letter are not significantly different at P = 0.05 (LSD).

(3) Efficacy against Seed-borne Phase of Mycosphaerella Blight in Field Pea

Mycosphaerella blight, caused by *Mycosphaerella pinodes,* is the most important disease of field pea throughout the world. The seed-borne phase of this disease is considered to be the major source of primary inoculum in the subsequent crop year. Seed treatment of infected seeds is essential for preventing the seed to seedling transmission and wide spread infections at the foliar stage during the plant development. In the present study, ACM941 seed treatment was evaluated for improving seedling emergence and yield of *M. pinodes* infected seeds of AC Tamor and Radley field peas, in comparison with thiram fungicide. Field experiments were conducted at AAFC Research Centre, Morden, Manitoba in 1995 and 1996 using infected seeds obtained from plants naturally infected with *M. pinodes* in 1994 and 1995, respectively. In each year, seeds of each cultivar were hand-separated into two categories: visibly poor (VP) seeds with lesions or shriveled due to the *M. pinodes* infection, and healthy-looking (HL) seeds without lesions and smooth. The percentage of seed infection by *M. pinodes was determined for* 200 randomly selected seeds from each category. Seed infection for VP seeds was 24% and 39% for AC Tamor and 37% and 46% for Radley, and for HL seeds was 9% and 10% for AC Tamor and 5% and 13% for Radley, harvested in 1994 and 1995, respectively. Seeds of each category were 54% in 1995 and 17% in 1996, and emergence of VP seeds by 208% in 1995 and 31% in 1996. Similarly. thiram increased emergence of HL seeds by 108% and 38%, and emergence of VP seeds by 293% and 55%. in 1995 and 1996, respectively.

All HL seeds produced a higher yield than did VP seeds in both 1995 and 1996 Table 13). On average of the two cultivars, ACM941 increased yield of HL seeds by 62% and 39%, and yield of VP seeds by 79% and 3%, in 1995 and 1996, respectively. Thiram increased yield of HL seeds by 106% in 1995, but decreased yield by 6% in 1996 and increased yield of VP seeds by 148% and 4% in 1995 and 1996, respectively.

Results of this study indicate that seed treatment with either ACM941 bioagent or thiram fungicide facilitates the expression of the inherent viability of these pea seeds. Comparison of ACM941 with the standard thiram seed treatment showed that ACM941 had overall a slightly lower emergence but greater yield increase. These results reflect the modes of action of the two seed treatments, as illustrated in previous examples. That is, ACM941 is effective in controlling a number of root rot fungal pathogens by mycoparasitism, and by colonizing the plant rhizosphere, therefore protecting plants from future pathogen infection. Thiram, on the other hand, is a protectant fungicide, which is fungitoxic to pathogens, but short lived.

TABLE 13

Comparative evaluation of ACM941 bioagent and thiram fungicide for the control of seed-borne phase of mycosphaerella blight in healthy looking (HL) and visibly poor (VP) seeds of field pea under field conditions in 1995 and 1996.

| | 1995 | | | | 1996 | | | |
|---|---|---|---|---|---|---|---|---|
| | AC Tamor | | Radley | | AC Tamor | | Radley | |
| | Emergence | Yield | Emergence | Yield | Emergence | Yield | Emergence | Yield |
| | Healthy-looking seed (HL) | | | | | | | |
| ACM941 | 52.1 ab* | 1470 b | 82.8 a | 532 a | 66.3 ab* | 8353 a | 74.9 ab | 4190 a |
| Thiram | 75.9 a | 2892 a | 91.0 a | 459 a | 77.9 a | 7381 a | 89.1 a | 3114 b |
| Nontreated | 31.0 b | 1228 b | 59.0 b | 260 a | 52.9 b | 7140 a | 69.5 b | 3666 ab |
| | Visibly poor seed (VP) | | | | | | | |
| ACM941 | 25.9 b | 175 a | 25.6 a | 472 a | 34.8 ab | 6982 a | 58.5 a | 4473 a |
| Thiram | 51.0 a | 260 a | 29.1 a | 643 a | 49.5 a | 7228 a | 57.5 a | 4410 a |
| Nontreated | 25.0 b | 248 a | 5.0 b | 165 b | 28.5 b | 6686 a | 42.1 b | 4442 a |

*Data in a column under each seed category followed by the same letter are not significantly different at P = 0.05 (LSD).

EXAMPLE 8

Compatibility and Comparative Evaluation of ACM941 Bioagent and Common Fungicides (1) Comparison and Compatibility of ACM941 with Thiram Fungicide Thiram 75WP which contains 75% thiram fungicide is a common seed treatment fungicide for seed decay, seedling blights and damping off of field crops, vegetables and ornamentals. In the present study, the effectiveness of ACM941 seed treatment was compared with thiram and rhizobium inoculant Self Stik™ in improving emergence and yield of field pea in field experiments conducted in two different geographic locations in Canada in 1996 and 1997. In addition, a seed treatment of ACM941 with a low rate of thiram was examined for its compatibility and a possible enhanced effectiveness. The experiments were set up on a sandy loam soil in Lacombe, Alberta and on a clay loam soil in Morden, Manitoba each year. Treatments of these experiments were ACM941 $10^7$ spores/mL at 5.0 mL/kg seed, Thiram 75WP at 1.0 g a.i./kg seed, Rhizobium Self Stik at 1.2 g/kg seed, and ACM941 plus 50% of the regular rate of thiram (0.5 g a.i./kg seed). Certified seed of two cultivars of field pea, Grande and Radley, was used in these experiments. The experiments were carried out in a split-plot design with cultivars in the main plots and treatments in the subplots, and four replicates per treatment, Plots were 4-row, 2.5 m long with 30 cm row spacing and 1.5 m apart between plots at the Lacombe site, and 3.0 m long with 30 cm row spacing and 1.2 m between plots at the Morden site. The seeding rate was 80 seeds per row for both locations in the two testing years. Standard management practices for each province were followed for weed control and fertilization of the crop. Emergence was counted for each plot 4 weeks after planting. Plants were harvested at maturity and the total seed yield and 1000-seed weight were collected when seeds were air dried to 13% seed moisture content High yielding potentials were achieved at the Lacombe site in both testing years (Table 14). Pea yield at the Lacombe site was significantly greater than that at the Morden site and the average yield of the field pea production in western Canada in both 1996 and 1997. Because of this high yielding potential, seed treatment effects were not clearly observed at the Lacombe site. On the average of the two cultivate and the two testing years, ACM941 increased emergence by 1%, and yield by 7% compared to the nontreated control. Under the same conditions, thiram increased emergence by 4%, but reduced yield by 4%, rhizobium reduced emergence by 4%, but increased yield by 9%, and ACM941 plus 50% of the regular rate of thiram increased emergence by 1%, and yield by 6%.

Alternatively, a relatively low yield potential was achieved at the Morden site (Table 14). Under such low yielding conditions, treatment effects were clearly observed. On the average of the two cultivars and the two testing years, ACM941 increased emergence by 13%, and yield by 32% compared to the nontreated control. Under the same conditions, thiram increased emergence by 38%, and yield by 29%, rhizobium increased emergence by 14%, and yield by 14%, and ACM941 plus 50% of the regular rate of thiram increased emergence by 34%, and yield by 36%.

On the average of the four station years, from the two different geographic sites in western Canada, ACM941 increased yield by 19% compared with nontreated controls. This effect was greater than thiram fungicide (12%) and the rhizobium inoculant (11%). ACM941 plus 50% of the regular rate of thiram was the most effective treatment, which increased yield by 21%. These results indicate that ACM941 bioagent had an equal or greater power in improving seedling emergence and yield in comparison with the common fungicide and rhizobium inoculant under both high and low yielding conditions. The results also indicated that ACM941 bioagent is compatible with thiram fungicide. An enhanced effectiveness was generally observed when ACM941 was combined with a low rate of thiram fungicide.

TABLE 14

Comparison and compatibility of ACM941 bioagent with thiram fungicide in efficacy of seed treatments under field conditions in 1996 and 1997.

| | 1996 | | | | 1997 | | | |
|---|---|---|---|---|---|---|---|---|
| | Grande | | Radley | | Grande | | Radley | |
| | Emergence | Yield | Emergence | Yield | Emergence | Yield | Emergence | Yield |
| | Lacombe, Alberta | | | | | | | |
| ACM941 (A) | 89.7 a* | 8759 a | 63.3 b | 5404 a | 77.2 a | 8550 a | 86.0 a | 5370 a |
| Thiram (T) | 87.2 a | 8729 a | 84.0 a | 5782 a | 67.0 b | 6507 b | 87.3 a | 4300 a |
| Rhizobium | 80.8 a | 8306 a | 61.0 b | 6401 a | 74.0 ab | 9426 a | 85.3 a | 4764 a |
| A + T † | 88.3 a | 8551 a | 71.8 ab | 6262 a | 71.3 ab | 8708 a | 85.7 a | 4599 a |
| Nontreated | 81.8 a | 8751 a | 69.3 ab | 5555 a | 73.0 ab | 8738 a | 90.7 a | 4082 b |
| | Morden, Manitoba | | | | | | | |
| ACM941 (A) | 47.1 a | 3319 a | 50.9 a | 3149 a | 66.7 a | 1735 a | 74.8 ab | 1785 a |
| Thiram (T) | 64.9 a | 4541 a | 74.1 a | 3286 a | 65.0 a | 1878 a | 79.1 a | 1064 c |
| Rhizobium | 49.9 a | 3650 a | 56.9 a | 2729 a | 59.8 b | 1710 a | 71.4 b | 1066 c |
| A + T † | 67.5 a | 3849 a | 66.6 a | 3495 a | 65.3 ab | 1793 a | 72.3 ab | 1595 b |
| Nontreated | 34.1 a | 3421 a | 49.6 a | 2766 a | 63.3 bc | 1128 c | 71.1 b | 1083 c |

*Data in a column under each location followed by the same letter are not significantly different at P = 0.05 (LSD).
† Thiuram was used at 50% of the regular rate.

(2) Comparison and Compatibility of ACM941 with Metalaxyl Fungicide

Apron FL which contains 31.7% metalaxyl fungicide is registered for pythium and phytophthora root rots, and downy mildew of field crops, vegetables and ornamentals. In the present study, the effectiveness of ACM941 seed treatment was compared with metalaxyl in controlling pythium root rot of field pea in field experiments conducted at AAFC Research Centre in Morden, Manitoba, in 1997 and 1998. In addition, a combination of metalaxyl with 10% of the regular rate of ACM941 was examined for its compatibility and a possible enhanced effectiveness. Treatments were ACM941 $10^7$ spores/mL at 5.0 mL/kg seed, Apron FL at 0.16 g a.i./kg seed, and Apron FL plus 10% of the regular rate of ACM941 ($10^6$ spores/mL at 5.0 mL/kg seed). Certified seed of Saturn field pea, which is highly susceptible to pythium root rot, was used in these experiments. The experiments were set up on a clay loam soil in 1997 and a sandy loam soil in 1998 with four replicates per treatment. The plot size, crop management and assessment methods used in these field experiments were the same as described above. The plots were inoculated with particles of vermiculite that had been moistened with 15% of V-8 juice solution at 5:1 of vermiculite:V-8 solution and infected with *Pythium aphanidermatum*. The infected vermiculite particles were incubated at 20° C. for 3–4 weeks, and distributed to the plot area at 50 mL/$m^2$ prior to the seeding.

The emergence and yield were much poorer, however, the treatment effects were greater in 1997 than 1998 (Table 15). On the average of the two testing years, treatments of ACM941 alone increased emergence by 16.5% and yield by 20.4%, compared to the nontreated controls. This effect was equal to or greater than those achieved with metalaxyl, which increased emergence by 17.3% and yield by 19.5%. An enhanced effectiveness was observed with the treatment of metalaxyl plus 10% of the regular rate of ACM941 bioagent, which increased the emergence by 21.2% and yield by 41.1%. These results coincided with previous findings that ACM941 bioagent had an equal or greater power in controlling pythium root rot and improving plant health and yield compared to the commercial fungicide. Results of this study also indicated that ACM941 bioagent is compatible with metalaxyl fungicide. An enhanced effectiveness was generally observed when ACM941 was combined with metalaxyl fungicide.

TABLE 15

Comparison and compatibility of ACM941 bioagent with mytalaxyl fungicide in efficacy of seed treatment under field conditions in 1997 and 1998.

| | 1997 | | 1998 | |
|---|---|---|---|---|
| Treatment | Emergence (%) | Yield (kg/ha) | Emergence (%) | Yield (kg/ha) |
| ACM941 | 45.1 a* | 1057 bc | 75.1 a | 5372 ab |
| Metalaxyl | 44.3 ab | 990 bc | 78.2 a | 5757 a |
| Metalaxyl + ACM941† | 46.6 a | 1362 a | 78.9 a | 5429 ab |
| Nontreated | 33.4 b | 755 c | 76.7 a | 5333 b |

*Data in the same column followed by the same letter are not significantly different at P = 0.05 (LSD).
†ACM941 was used at 10% of the regular rate.

EXAMPLE 9

Liquid Fermentation of ACM941 Bioagent

As the first step of industrial production of ACM941 bioagent, a series of nine experiments were conducted to determine the optimum conditions for fermenting ACM941 bioagent at Agriculture and Agri-Food Canada Research Centre, Morden, Manitoba in 1996–1997. Various media were prepared and added to 125-mL Erlenmeyer flasks with cotton and cheesecloth plugs at 50 mL medium per flask and three replicate flasks per treatment. These flasks were autoclaved for 15 minutes at 121° C. and 21 psi. Each flask was then inoculated with a disc of ACM941 cut with 5-mm-diameter cork borer from the edge of 4 week old culture of ACM941 bioagent on potato dextrose agar (PDA). Flasks were shaken continuously on an orbital shaker at 110 rpm at 20° C., under 16-h light and 8-h dark at 24 $uEm^{-2}s^{-1}$ light intensity. Sporulation was assessed at 4 and 7 days after inoculation, respectively.

In experiment I, six carbon sources, including four simple carbohydrates (glucose, maltose, malt extract, sucrose) and two complex carbon or nutrient sources (glycerol, yeast extract+glucose) were tested for their effects on spore production in the basal Czapek's salt medium (BCSM). These carbon sources were added to BCSM at the rate of 20 g/L for the simple carbohydrates and at 10 g/L for the complex carbon or nutrient soures. Of the six carbon sources tested, malt extract in BCSM had the greatest sporulation, which was nearly 10-fold greater than any other carbon sources tested (Table 16).

In experiment II, Malt extract alone and in combination with BCSM were tested. Malt extract alone provided an equal to or greater level of spore production than that of malt extract plus BCSM (Table 16). BCSM was thereafter not used in further fermenting experiments.

In experiment III, eight concentrations of malt extract medium (5 g/L, 10 g/L, 20 g/L, 30 g/L, 40 g/L, 60 g/L, 80 g/L, and 120 g/L) were tested for their effects on ACM941 spore production. The treatment of 120 g/L of malt extract had the greatest spore production but not significantly different from treatments of 40 g/L, 60 g/L and 80 g/L (Table 16). The concentration of 40 g/L of malt extract was thereafter used in further experiments.

In experiment IV, initial inocula of ACM941 from five different sources were evaluated for their sporulation potential in 40 g/L malt extract broth medium. These treatments were: 1) mycelium from the growing edge of a 1 week-old culture on water agar (WA-1 wk); 2) mycelium from the growing edge of a 2 week-old culture on PDA (PDA-mycelium-2 wk); 3) mycelium with minimal sporulation from the edge of a 4 week-old culture on PDA (PDA-mycelium-4 wk). 4) clumps of sporulating mycelium from the edge of 4 week-old culture on PDA (PDA-spore-edge-4 wk); and 5) sporulating mycelium from the center of a 4 week-old culture on PDA (PDA-spore-centre-4 wk). Of the five different initial inocula of ACM941 bioagent tested, PDA-spore-edge-4 wk and PDA-spore-centre-4 wk had equal and significantly greater potential in sporulation than other treatments (Table 16), and were thereafter used in further experiments, In experiment V, different aeration conditions were tested for their effect on sporulation potential of ACM941 in 40 g/L malt extract broth medium using three different sizes of Erlenmeyer flasks (125 mL, 250 mL, and 500 mL) with two speeds of agitation (90 rpm and 110 rpm). Treatment with 125 mL Erlenmeyer flask shaken at 90 rpm had a significantly higher level of spore production than other treatments (Table 16). The results indicate that a reduced aeration would have a positive impact on sporulation, which facilitates increased volumes in an industrial fermentation process, In experiment VI, three light intensity levels were evaluated for their effect on sporulation potential of ACM941 in 40 g/L malt extract broth medium. These treatments were: 1) direct lighting at 24 $uEm^{-2}s^{-1}$; 2) ambient room light at 10 $uEm^{-2}s^{-1}$; and 3) dark (flasks covered with tin foil and placed with ambient light treatment). The direct lighting treatment had greatest spore production compared to other treatments, but was not significantly different from ambient light treatment (Table 16). Dark treatment had the lowest spore production, indicating that light is required for the optimum spore production of ACM941 bioagent.

In experiment VII, five initial pH levels (3.0, 3.5, 4.5 (pH of non-adjusted medium), 5.5, and 7.0) of the malt extract medium were tested for their effects on sporulation of ACM941. The various levels of pH were adjusted using Fisher Brand pH meter by adding 1 N HCl or NaOH solution before the fermentation process. Treatments with initial pH of 4.5 (not adjusted malt extract broth medium) and pH adjusted to 7.0 had the similar greatest level of sporulation compared to other pH levels tested (Table 16). The non-adjusted pH level (4.5) of malt extract medium was thereafter used in further experiments.

In experiment VIII, two temperatures (20° C. and 30° C.) and two malt extract concentrations (20 g/L and 40 g/L) were tested for their combined effects on ACM941 sporulation. Treatment of 40 g/L malt extract broth at 30° C. had the greatest spore production and was significantly different from other treatments (Table 16), indicating that the relatively high temperature may have a positive impact on the sporulation.

In experiment IX, three temperatures (25° C., 30° C., and 33° C.), two malt extract concentrations (40 g/L and 120 g/L) and two light intensities (24 $uEm^{-2}s^{-1}$ and 60 $uEm^{-2}s^{-1}$) were tested for their combined effects on ACM941 sporulation. Due to the technical constraint, the light intensity of 24 $uEm^{-2}s^{-1}$ was provided only at 25° C. and 60 $uEm^{-2}s^{-1}$ light intensity at 30° C. and 33° C. Treatment of 40 g/L malt extract broth at 25° C. and with light intensity of 24 $uEm^{-2}s^{-1}$ had the greatest spore production compared to other treatments (Table 16). Treatments with 120 g/L did not produce the higher sporulation than treatments with 40 g/L as observed in previous experiments. The treatment of 40 g/L of malt extract at 30° C. had also not provided higher sporulation potential as observed earlier. These may have been due to the inhibitory effect of the higher light intensity used (60 $uEm^{-2}s^{-1}$) for treatments with 30° C. and 33° C. These results suggest that temperatures of 30° C. or lower and fight intensity of less than 60 $uEm^{-2}s^{-1}$ are required for an optimum spore production.

The results of these fermenting experiments suggest that ACM941 can be effectively produced using inexpensive media. Based on this information, Chr. Hansen BioSystems in Milwaukee, Wis. produced the first batch of 40 g of freeze-dried commercial preparation of ACM941 in their pilot-plant in March 1999. These results suggest that large-scale fermentation of ACM941 for the purpose of industrial production would be easily attainable.

TABLE 16

Factors affecting spore productivity of ACM941 bioagent in liquid fermentation experiments.

| Experiment no. | Treatment | 4 day (× 10,000 spores/mL) | 7 day (× 10,000 spores/mL) |
|---|---|---|---|
| I | Glucose + BCSM | 16.7 b* | 10.9 b |
| | Glycerol + BCSM | 0.4 b | 0.3 b |
| | Malt extract + BCSM | 135.7 a | 200.8 a |
| | Maltose + BCSM | 11.2 b | 3.6 b |

TABLE 16-continued

Factors affecting spore productivity of ACM941 bioagent in liquid fermentation experiments.

| Experiment no. | Treatment | 4 day (× 10,000 spores/mL) | 7 day (× 10,000 spores/mL) |
|---|---|---|---|
| | Sucrose + BCSM | 8.3 b | 1.4 b |
| | Yeast + glucose + BCSM | 0.1 b | 0.8 b |
| II | Malt extract | 107.7 b | 504.2 a |
| | Malt extract + BCSM | 401.7 a | 367.8 a |
| III | Malt extract 5 g/L | 15.7 b | 11.0 b |
| | Malt extract 10 g/L | 26.8 b | 24.0 b |
| | Malt extract 20 g/L | 53.6 b | 31.8 b |
| | Malt extract 30 g/L | 108.8 ab | 60.3 b |
| | Malt extract 40 g/L | 99.7 ab | 120.5 ab |
| | Malt extract 60 g/L | 88.3 ab | 102.7 ab |
| | Malt extract 80 g/L | 110.5 ab | 157.1 ab |
| | Malt extract 120 g/L | 341.4 a | 573.0 a |
| IV | PDA-myceluim-2 week | 47.7 c | 75.1 c |
| | PDA-myceluim-4 week | 65.8 bc | 127.1 bc |
| | PDA-spore-edge-4 week | 125.3 a | 247.7 a |
| | PDA-spore-center-4 week | 112.3 ab | 218.4 ab |
| | WA-1 week | 48.7 c | 81.5 c |
| V | 125 mL flask, 110 rpm | 131.4 bc | 268.7 b |
| | 125 mL flask, 90 rpm | 329.7 a | 515.6 a |
| | 250 mL flask, 110 rpm | 168.5 b | 172.4 bc |
| | 250 mL flask, 90 rpm | 83.2 bc | 137.3 bc |
| | 500 mL flask, 110 rpm | 54.5 c | 15.0 c |
| | 500 mL flask, 90 rpm | 37.0 c | 99.5 bc |
| VI | Direct light 24 $uEm^{-2}s^{-1}$ | 70.8 a | 114.1 a |
| | Ambient light 10 $uEm^{-2}s^{-1}$ | 51.7 b | 84.9 a |
| | Dark | 42.5 b | 24.1 b |
| VII | Malt extract pH 3.0 | 1.3 b | 1.2 b |
| | Malt extract pH 3.5 | 6.7 b | 24.0 b |
| | Malt extract pH 4.5 (non-adjusted) | 130.3 a | 223.3 a |
| | Malt extract pH 5.5 | 64.1 ab | 91.5 ab |
| | Malt extract pH 7.0 | 138.7 a | 192.2 a |
| VIII | Malt extract 20 g/L, 20° C. | 39.3 b | 48.8 b |
| | Malt extract 40 g/L, 20° C. | 47.8 b | 69.9 b |
| | Malt extract 20 g/L, 30° C. | 99.8 b | 72.3 b |
| | Malt extract 40 g/L, 30° C. | 502.7 a | 289.8 a |
| IX | Malt extract 40 g/L, 25° C., 24 $uEm^{-2}s^{-1}$ | 28.4 a | 28.3 a |
| | Malt extract 120 g/L, 25° C., 24 $uEm^{-2}s^{-1}$ | 12.7 bc | 12.5 b |
| | Malt extract 40 g/L, 30° C., 60 $uEm^{-2}s^{-1}$ | 6.8 c | 15.4 b |
| | Malt extract 120 g/L, 30° C., 60 $uEm^{-2}s^{-1}$ | 11.8 bc | 17.7 b |
| | Malt extract 40 g/L, 33° C., 60 $uEm^{-2}s^{-1}$ | 23.2 ab | 17.6 b |
| | Malt extract 120 g/L, 33° C., 60 $uEm^{-2}s^{-1}$ | 10.6 bc | 5.1 c |

*Data in a column followed by the same letter in each experiment are not significantly different at P = 0.05 (LSD).

EXAMPLE 10

Effect of Media and Fermentation Methods on the Efficacy of ACM941 Seed Treatments A comparative evaluation of ACM941 bioagent, produced from liquid fermentation (LF) and solid medium (SM), for their efficacy in seed treatment was conducted in growth room experiments at AAFC Research Centre, Morder, Manitoba in 1997. ACM941 spore suspension from SM was prepared by washing the colony of a 4 week old culture, grown on PDA medium. ACM941 spore suspension from LF was prepared from 5 day-old 4% malt extract broth, concentrated by centrifugation for 10 min. at 2000 rpm at 4° C., and resuspended in 0.1% Tween 20. The suspensions were tested on AC Tamor field pea seeds, which were harvested in 1996 from fields that were severely affected by mycosphaerella blight, moderately affected by Fusarium wilt and powdery mildew. Seeds were treated with the spore suspensions at $10^7$ spores/mL and 5.0 mL/kg seed. Seeds were planted at 6 hours and 24 days after treatment in wood planting flats (35.5×47.0 cm) containing soil mixture of 2:1:1 of soil, perlite and peat moss. For each planting, 40 seeds were planted in each of the 4 replicate flats for each treatment, Remaining treated seeds were kept in a 3.7° C. walk-in refrigerator between the plantings. The planted flats were placed in a growth cabinet maintained at 20° C., with a 14-h photoperiod at 350 $mol.m^{-2}.s^{-1}$ light intensity by fluorescent and incandescent lamps. Emergence was counted 7 days after planting and disease severity was rated 14 days after planting using the 0–9 scale described above.

ACM941 spores produced from both LF and SM were effective in increasing emergence and reducing the root rot severity when used as seed treatments (Table 17). In comparison with the nontreated controls, ACM941 from LF increased emergence by 148% and 116% when planted 6 hours and 24 days after seeds were treated, respectively. These effects were equal to those achieved with ACM941 spores produced from SM, which increased emergence by 92% and 144%, at 6 hours and 24 days after seeds were treated, respectively, Neither ACM941 LF nor ACM941 SM treatments showed effects in reducing root rot severity when seeded the same day after seed treatment. However, both treatments reduced the root rot severity by 18% when seeded 24 days after the seed treatment. A reduced effect was not observed after seeds were treated and stored for 24 days. The findings of this experiment coincide with the previous results which indicate that ACM941 bioagent has a long shelf life on seeds.

TABLE 17

Comparative evaluation of ACM941 spores produced from liquid fermentation (LF) and from solid medium (SM) and timings of post seed treatment on efficacy of seed treatments in field pea.

| | 6 hours after seed treatment | | 24 days after seed treatment | |
|---|---|---|---|---|
| Treatment | Emergence (%) | Root rot severity (0–9) | Emergence (%) | Root rot severity (0–9) |
| ACM941 SM | 55.0 b* | 4.8 a | 92.5 a | 3.2 a |
| ACM941 LF | 71.2 a | 3.1 ab | 67.5 b | 3.2 a |
| Nontreated | 28.7 c | 3.1 b | 31.2 c | 3.9 a |

*Data in a column followed by the same letter are not significantly different at P = 0.05 (LSD).

REFERENCES

1. Baker, K. F. 1987. Evolving Concepts of Biological Control of Plant Pathogens. Ann. Rev. Phytopathol. 25:67–85.
2. Cook, R. J., and K. F. Baker. 1983. The nature and practice of biological control of plant pathogens. APS Press, ST. Paul, Minn. 539 pp.
3. Hwang, S. F., and P. Chakravarty. 1993. Integrated biological and chemical control of Rhizoctonia root rot of field pea by *Gliocladium virens* and a fugicide. J. Plant Dis. Prot. 100:308–316.
4. Parke, J. L., R. E. Rand, A. E. Joy, A. E. King. 1991. Biological control of Pythium damping-off and Aphanomyces root rot of peas by application of *Pseudomonas cepacia* or *P. fluorescens* to seed. Plant Dis. 75:987–992.
5. Nelson, E. B., G. E. Harman and G. T. Nash. 1988, Enhancement of Trichoderma-induced biological control of Pythium seed rot and pre-ernergence damping-off of peas. Soil Bio. Biochem. 20:145–150.
6. Windels, C. E, and T. Kommedahl. 1982. Pea cultivar effect on seed treatment with *Penicillium oxalicum* in the field. Phytopathology 72,541–43.
7, Oyarzun, P. J., J. Postma, A. J. G. Luttikholt, and A. E. Hoogland. 1994. Biological control of foot and root rot in pea caused by *Fusarium solani* with nonpathogenic *Fusarium oxysporum* isolates. Can. J. Bot. 72;843–852.
8. Xi, K., J. H. G. Stephens, and P. R. Vera. 1996. Application of formulated rhizobacteria against root rot of field pea. Plant Pathol. 45:1150–1158.
9. Steinmetz, J. and Schonbeck, F. 1994. Conifer bark as growth medium and carrier for *Trichoderma harzianum* and *Gliocladium roseum* to control *Pythium ultimum* on pea. Zeitschrift fur Pflanzenkrankheiten und Pflanzenschutzby 101:200–211.
10, Harman, E. E., I. Chet, and R. Baker. 1980. *Trichoderma hamatum* effects on seed and seedling disease induced in radish and pea by Pythium spp. or *Rhizoctonia solani.* Phytopathology 70:1167–1172.
11. Tu, J. C. 1992. Management of root rot diseases of peas, beans, and tomatoes. Can. J. Plant Pathol. 14:92–99.
12. Ainsworth, G. C., F. K. Sparrow, and A. S. Sussman. 1973. The Fungi. An advanced Treatise. Vol. IVA. A taxonomic review with keys: Ascomycetes and Fungi Imperfect. Academic Press, New York. 621 pp.
13. Booth, C, 1971. Methods in Microbiology. Vol. 4. Academic Press, New York. 795 pp.
14. Barnett, H. L., and B. B. Hunter. 1972. Illustrated Genera of Imperfect Fungi. Burgess Publishing, Minneapolis, Minn. 241 pp.
15. Jones, D., D. Vaughan, and W. J. McHardy. 1992. Scanning electron microscopy of a soil fungus *Gliocladium roseum.* Scanning Microscopy 6: 591–596.
16. Domsch, K. H., W. Gams, and T.-H. Anderson. 1980. Compendium of Soil Fungi. Academic Press, London. 377pp.
17. Pugh, G. J. F., and C. H. Dickinson. 1965. Studies on fungi in coastal soils. VI. *Gliocladium roseum* bainier. Trans. Brit. Mycol. Soc. 48: 279–285.
18. Seifert, K. 1985. A monograph of Stilbella and some allied hyphomycetes. Studies in Mycol. 27:1–235.
19. Lees, S. B. and Taylor, J. W. 1990. Isolation of DNA from fungal mycelium and single spores. Pages 282–287 in M. A. Innis, D. H. Gelfand and J. J. Sninsky, eds., PCR Protocols—A guide to methods and applications, Academic Press, San Diego, Calif.
20. Park, Y. H., J. P. Stack and C. M. Kenerley, 1992. Selective isolation and enumeration of *Gliocladium virens* and *G. roseum* from soil. Plant Dis. 76: 230–235.
21. Farr, D. F., G. F. Bills, G. P. Chamuris, and A. Y. Rossman. 1989. Fungi on plants and plant products in the United States. APS Press, St. Paul, Minn. 1252 pp.

What is claimed is:

1. A biologically pure culture of a strain of a microorganism *Gliocladium roseum* exhibiting antagonistic effects against a plant pathogen, said microorganism having the identifying characteristics of ATCC #74447.

2. The culture of claim 1, having antagonistic effects against at least one pathogen selected from the groups of Ascomycetes, Deuteromycetes, Oomycetes and Zygomycetes.

3. The culture of claim 1, wherein the microorganism is capable of protection against fungal pathogens causing seed decay, foot/root rots, seedling blight, head blight and wilt diseases in plants of Asteraceae, Brassicaceae, Chenopodiaceae, Cucurbitaceae, Fabaceae, Poaceae and Solanaceae.

4. The culture of claim 1, wherein the microorganism is capable of protection against are soil-borne and seed-borne *Rhizoctonia solani* on pea, bean, beet, canola, broccoli, brussel sprouts, cabbage, cauliflower, cucumber, egg plant, pepper, tomato and marigold, soil-borne and seed-borne *Alternaria alternata, Aphanomyces euteiches,* Ascochyta spp., *Fusarium oxysporum, Fusarium solani, Mycosphaerella pinodes, Pythium aphanidermatum, Pythium ultimum,* Rhizopus sp., and *Sclerotinia sclerotiorum* on pea, and soil-borne and seed-borne *Bipolaris sorokiniana* and *Fusarium graminearum* on wheat and barley.

5. A composition comprising:

a culture of a strain of *Gliocladium roseum* exhibiting antagonistic effects against a plant pathogen, said strain of *Gliocladium roseum* having the identifying characteristics of ATCC #74447; and a delivery medium.

6. The composition of claim 5, wherein the delivery medium is a plant seed.

7. The composition according to claim 6, wherein the seed is chosen from the group consisting of seeds of wheat, seeds of barley, seeds of canola, seeds of sugar beet, seeds of table beet, seeds of dry bean, seeds of garden bean, seeds of field pea, seeds of sweet pea, seeds of broccoli, seeds of brussel sprouts, seeds of cabbage, seeds of cauliflower, seeds of cucumber, seeds of egg plant, seeds of pepper, seeds of tomato, and seeds of marigold.

8. The composition according to claim 5, including at least one fungicide.

9. The composition according to claim 8, wherein the at least one fungicide is at least one fungicide intended for use with field crops, horticultural crops, vegetables or ornamentals.

10. A method of protecting a plant from fungal infection comprising the steps of contacting the plant during a stage of the growth of said plant or contacting a seed of said plant with a strain of a microorganism *Gliocladium roseum* exhibiting antagonistic effects against a fungal plant pathogen, said strain having the identifying characteristics of ATCC #74447.

11. The method of claim 10, wherein the seed of said plant is immersed into a composition comprising said strain before said seed is planted in a growth medium for said plant and said plant is grown.

12. The method according claim 10 wherein said plant comprises plant seedlings or seeds and said plant is planted in a growth medium containing said strain.

13. A method of protecting pea plants against PRRC pathogens, said method comprising: isolating a culture of a strain of a microorganism *Gliocladium roseum* exhibiting antagonistic effects against fungal plant pathogens, said strain having the identifying characteristics of ATCC #74447; treating a seed with said strain of said microorganism; and planting said seed in a soil environment.

14. A biologically pure culture of a strain of a microorganism *Gliocladium roseum* exhibiting antagonistic effects against a plant pathogen, characterized by bands of 1.3 kb following DNA amplification with UBC519 primer and of 0.5 kb and 1.3 kb following DNA amplification with UBC521 primer.

15. The culture of claim 14, having antagonistic effects against at least one pathogen selected from the groups of Ascomycetes, Deuteromycetes, Oomycetes and Zygomycetes.

16. The culture of claim 14, wherein the microorganism is capable of conferring protection against fungal pathogens causing seed decay, foot/root rots, seedling blight, head blight and wilt diseases in plants of Asteraceae, Brassicaceae, Chenopodiaceae, Cucurbitaceae, Fabaceae, Poaceae and Solanaceae.

17. The culture of claim 14, wherein the microorganism is capable of conferring protection against are soil-borne and seed-borne *Rhizoctonia solani* on pea, bean, beet, canola, broccoli, brussel sprouts, cabbage, cauliflower, cucumber, egg plant, pepper, tomato and marigold, soil-borne and seed-borne *Alternaria alternate, Aphanomyces euteiches,* Ascochyta spp., *Fusarium oxysporum, Fusarium solani, Mycosphaerella pinodes, Pythium aphanidermatum, Pythium ultimum*, Rhizopus sp., and *Sclerotinia sclerotiorum* on pea, and soil-borne and seed-borne *Bipolaris sorokiniana* and *Fusarium graminearum* on wheat and barley.

18. A composition comprising:

a culture of a strain of *Gliocladium roseum* exhibiting antagonistic effects against a plant pathogen, characterized by bands of 1.3 kb following DNA amplification with UBC519 primer and of 0.5 kb and 1.3 kb following DNA amplification with UBC521 primer; and a delivery medium.

19. The composition of claim 18, wherein the delivery medium is a plant seed.

20. The composition according to claim 19, wherein the seed is chosen from the group consisting of seeds of wheat, seeds of barley, seeds of canola, seeds of sugar beet, seeds of table beet, seeds of dry bean, seeds of garden bean, seeds of field pea, seeds of sweet pea, seeds of broccoli, seeds of brussel sprouts, seeds of cabbage, seeds of cauliflower, seeds of cucumber, seeds of egg plant, seeds of pepper, seeds of tomato, and seeds of marigold.

21. The composition according to claim 18 including at least one fungicide.

22. The composition according to claim 18, wherein the at least one fungicide is at least one fungicide intended for use with field crops, horticultural crops, vegetables or ornamentals.

23. A method of protecting a plant from fungal infection comprising contacting a plant during a stage of the growth of said plant with a strain of a microorganism *Gliocladium roseum* exhibiting antagonistic effects against a fungal plant pathogen, characterized by bands of 1.3 kb following DNA amplification with UBC519 primer and of 0.5 kb and 1.3 kb following DNA amplification with UBC521 primer.

24. The method of claim 23, wherein a seed of said plant is immersed into a composition comprising said strain before said seed is planted in a growth medium for said plant and said plant is grown.

25. The method according to claim 23 wherein said plant comprises plant seedlings or seeds and said plant is planted in a growth medium containing said strain.

26. A method of protecting pea plants against PRRC pathogens, said method comprising: isolating a culture of a strain of a microorganism *Gliocladium roseum* exhibiting antagonistic effects against fungal plant pathogens characterized by bands of 1.3 kb following DNA amplification with UBC519 primer and of 0.5 kb and 1.3 kb following DNA amplification with UBC521 primer; treating a seed with said strain of said microorganism; and planting said seed in a soil environment.

* * * * *